US011471201B2

(12) United States Patent
Ferrero Manzanal et al.

(10) Patent No.: US 11,471,201 B2
(45) Date of Patent: Oct. 18, 2022

(54) CEPHALOMEDULLARY NAILING SYSTEM OF VARIABLE ANGLE TO TREAT FEMUR FRACTURES AND THE UTENSILS USED TO PLACE THE SYSTEM

(71) Applicants: Francisco Ferrero Manzanal, Cartagena (ES); Antonio Murcia Asensio, Torrevieja (ES)

(72) Inventors: Francisco Ferrero Manzanal, Cartagena (ES); Antonio Murcia Asensio, Torrevieja (ES)

( * ) Notice: Subject to any disclaimer, the term of this patent is extended or adjusted under 35 U.S.C. 154(b) by 485 days.

(21) Appl. No.: 16/340,482

(22) PCT Filed: Oct. 10, 2016

(86) PCT No.: PCT/ES2016/000110
§ 371 (c)(1),
(2) Date: Apr. 9, 2019

(87) PCT Pub. No.: WO2018/069554
PCT Pub. Date: Apr. 19, 2018

(65) Prior Publication Data
US 2019/0380752 A1    Dec. 19, 2019

(51) Int. Cl.
*A61B 17/74* (2006.01)
*A61B 17/88* (2006.01)
(Continued)

(52) U.S. Cl.
CPC .......... *A61B 17/744* (2013.01); *A61B 17/151* (2013.01); *A61B 17/164* (2013.01);
(Continued)

(58) Field of Classification Search
CPC . A61B 17/744; A61B 17/746; A61B 17/7233; A61B 17/725
See application file for complete search history.

(56) References Cited

U.S. PATENT DOCUMENTS 4,697,585 A * 10/1987 Williams ............... A61B 17/72
606/64
5,281,224 A * 1/1994 Faccioli ............. A61B 17/1725
606/62
(Continued)

FOREIGN PATENT DOCUMENTS

DE    102007029090 A1 * 12/2008 .......... A61B 17/744
EP       1 072 229 A2 *  7/2000
(Continued)

OTHER PUBLICATIONS

International Search Report dated Jun. 20, 2017 in corresponding International application No. PCT/ES2016/000110; 9 pages.
(Continued)

*Primary Examiner* — Ellen C Hammond
(74) *Attorney, Agent, or Firm* — Maier & Maier, PLLC

(57) ABSTRACT

The cephalomedullary nailing system of this invention contributes to solving three main problems: reduce fractures, improve assembly biomechanics to ensure the load axis is favorable as possible for bony fragments and prevent femoral neck collapse as well as offset and limb length loss, hence avoiding the possibility of reduced abductor power. The system is based on specific screw channel geometry and the placement of an additional locking screw, allowing the nail to turn 360° and facilitating nail insertion through the screw.

12 Claims, 30 Drawing Sheets

(51) Int. Cl.
*A61B 17/90* (2006.01)
*A61B 17/15* (2006.01)
*A61B 17/16* (2006.01)
*A61B 17/17* (2006.01)

(52) U.S. Cl.
CPC ...... *A61B 17/1615* (2013.01); *A61B 17/1717* (2013.01); *A61B 17/746* (2013.01); *A61B 17/8872* (2013.01); *A61B 17/90* (2021.08); *A61B 2017/1602* (2013.01)

(56) References Cited

U.S. PATENT DOCUMENTS

| | | | | |
|---|---|---|---|---|
| 6,562,042 | B2 * | 5/2003 | Nelson | A61B 17/1721 |
| | | | | 606/328 |
| 8,834,469 | B2 * | 9/2014 | Watanabe | A61B 17/7233 |
| | | | | 606/64 |
| 8,906,023 | B2 * | 12/2014 | Matityahu | A61B 17/7241 |
| | | | | 606/64 |
| 9,289,220 | B2 * | 3/2016 | Wolfe | A61B 17/1717 |
| 9,517,094 | B1 * | 12/2016 | Savage | A61B 17/744 |
| 10,123,828 | B2 * | 11/2018 | Matityahu | A61B 17/744 |
| 2002/0156473 | A1 * | 10/2002 | Bramlet | A61B 17/744 |
| | | | | 606/62 |
| 2010/0234846 | A1 * | 9/2010 | Eglseder | A61B 17/72 |
| | | | | 606/62 |
| 2016/0310176 | A1 * | 10/2016 | Van Dyke | A61B 17/72 |

FOREIGN PATENT DOCUMENTS

| | | | | |
|---|---|---|---|---|
| EP | 1 072 229 | A2 | 1/2001 | |
| EP | 2 730 243 | A1 | 5/2014 | |
| EP | 2730243 | A1 * | 5/2014 | ........ A61B 17/744 |
| FR | 2 997 837 | | * 11/2012 | |
| WO | 01/56487 | A1 | 8/2001 | |

OTHER PUBLICATIONS

Written Opinion of the International Searching Authority dated Jun. 20, 2017 in corresponding International application No. PCT/ES2016/000110; 7 pages.

International Preliminary Report on Patentability dated Feb. 11, 2019 in corresponding International application No. PCT/ES2016/000110; 10 pages.

* cited by examiner

AB-based cutting

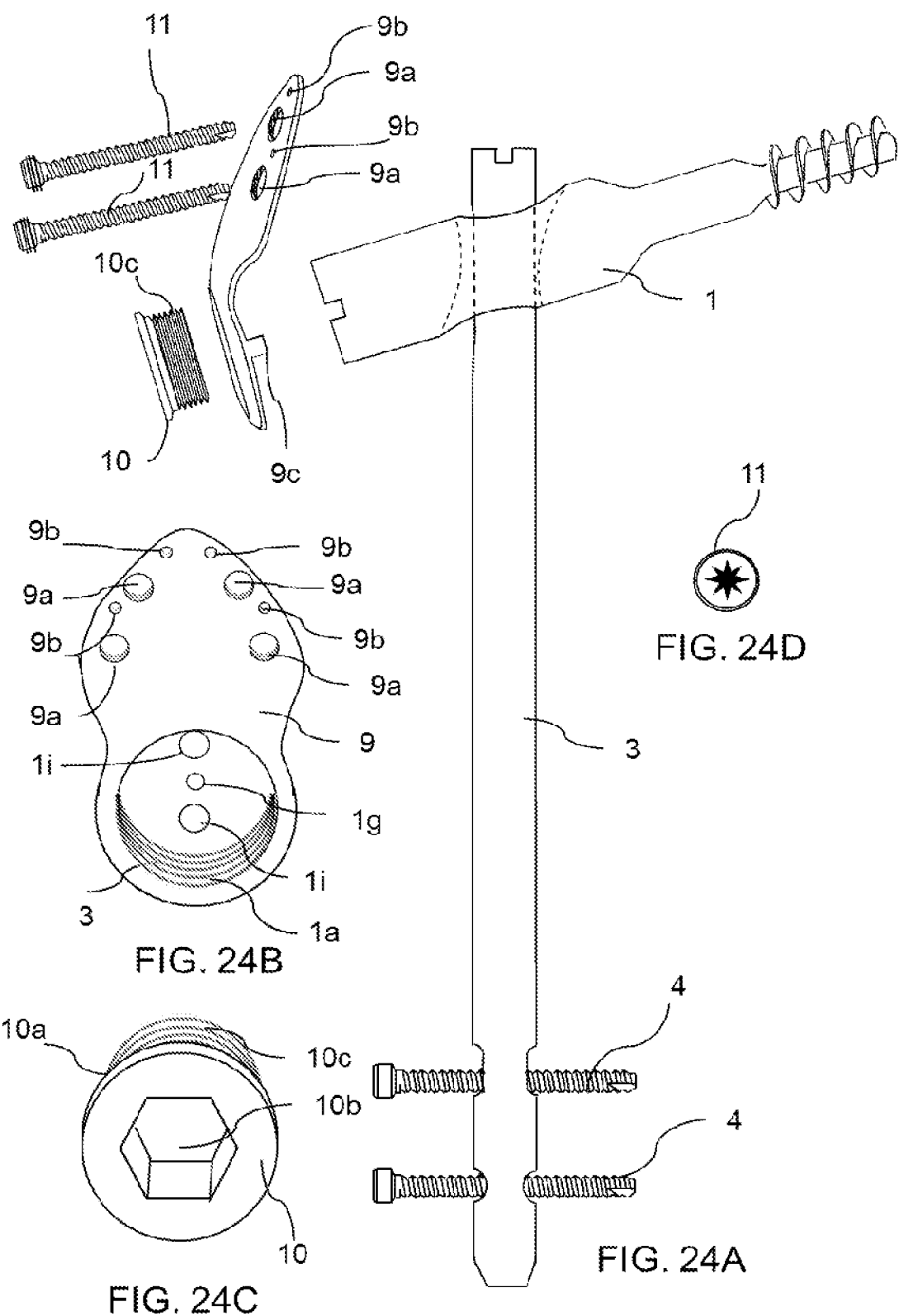

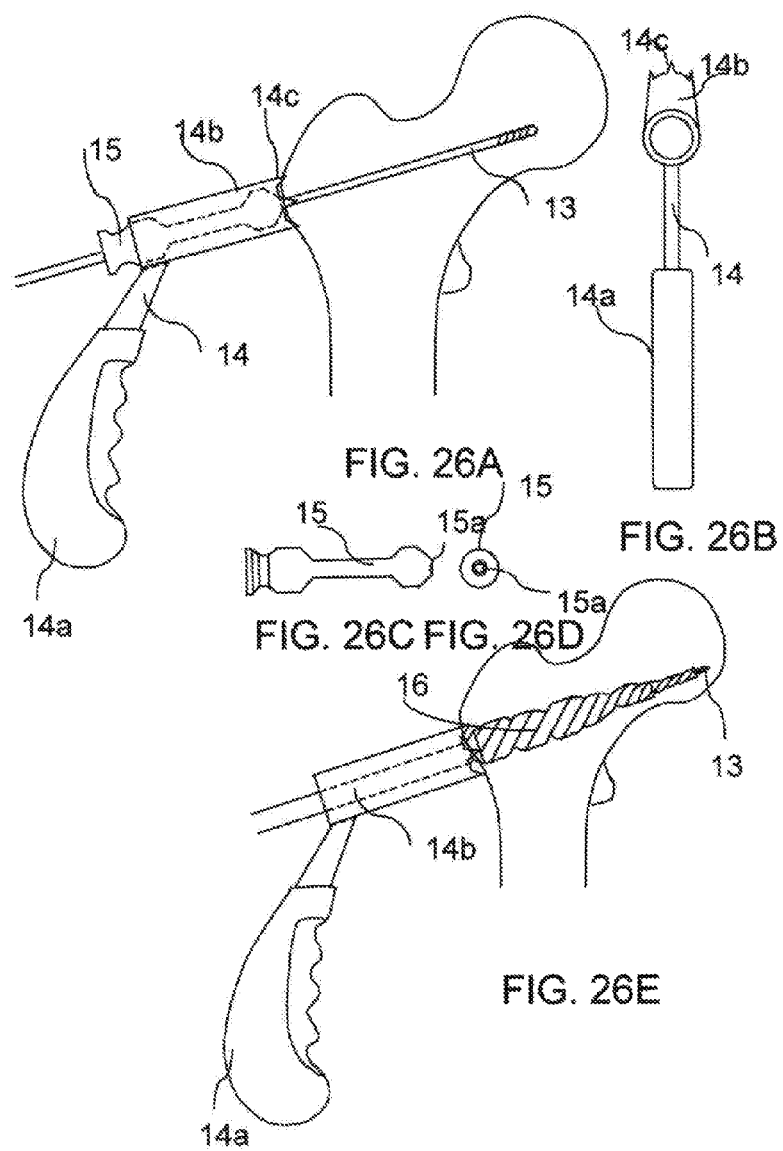

AB-based cutting

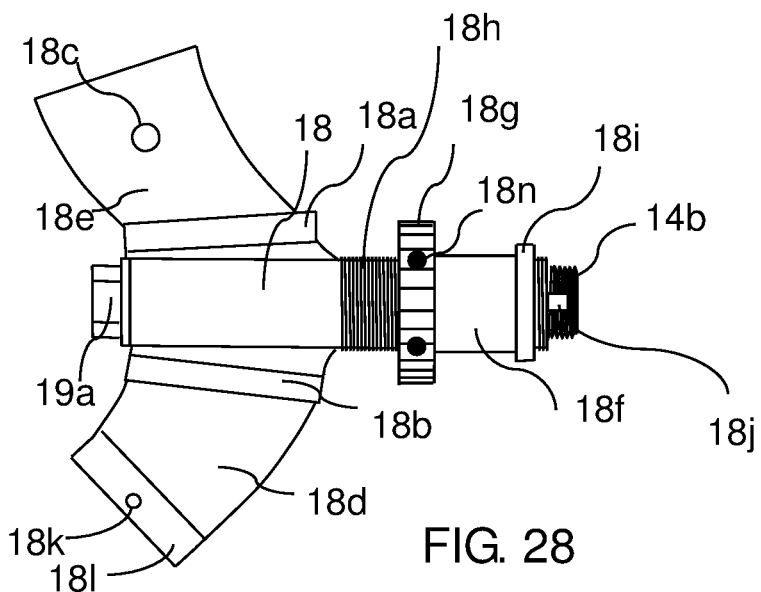
FIG. 28
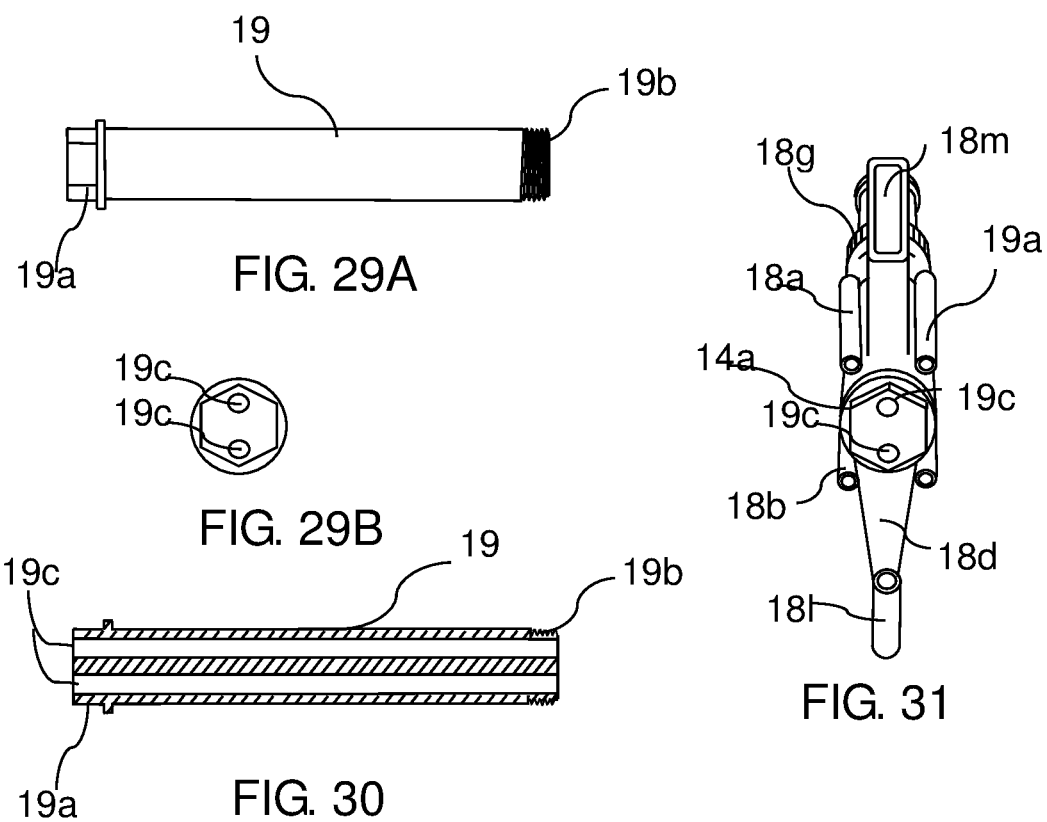
FIG. 29A
FIG. 29B
FIG. 30
FIG. 31

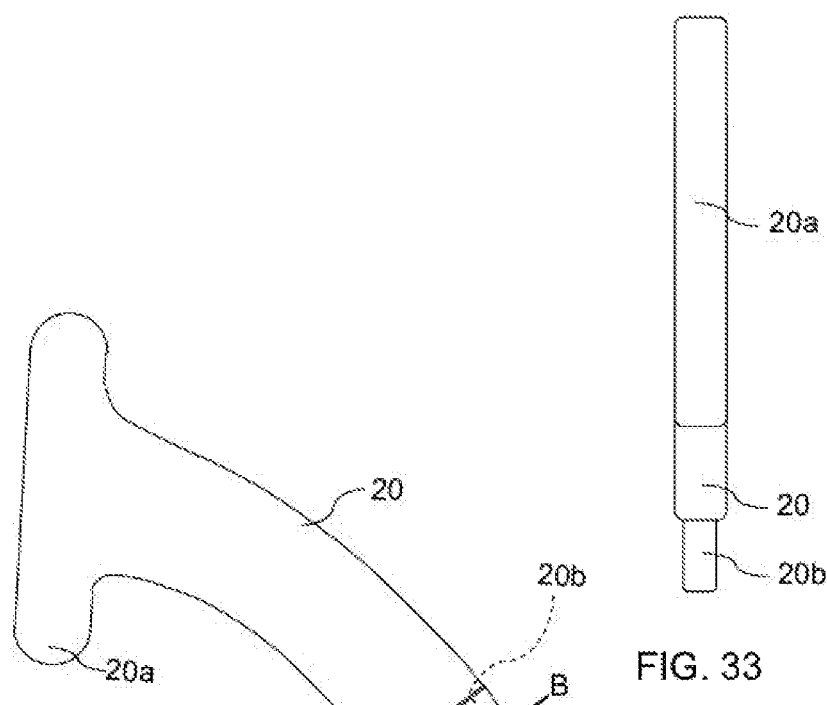
FIG. 33
FIG. 32
AB-based cutting
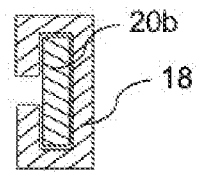
FIG. 34
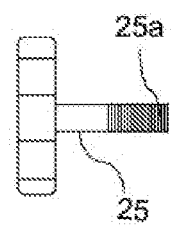 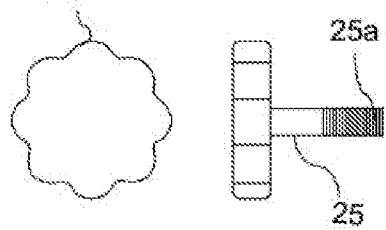
FIG. 35A   FIG. 35B

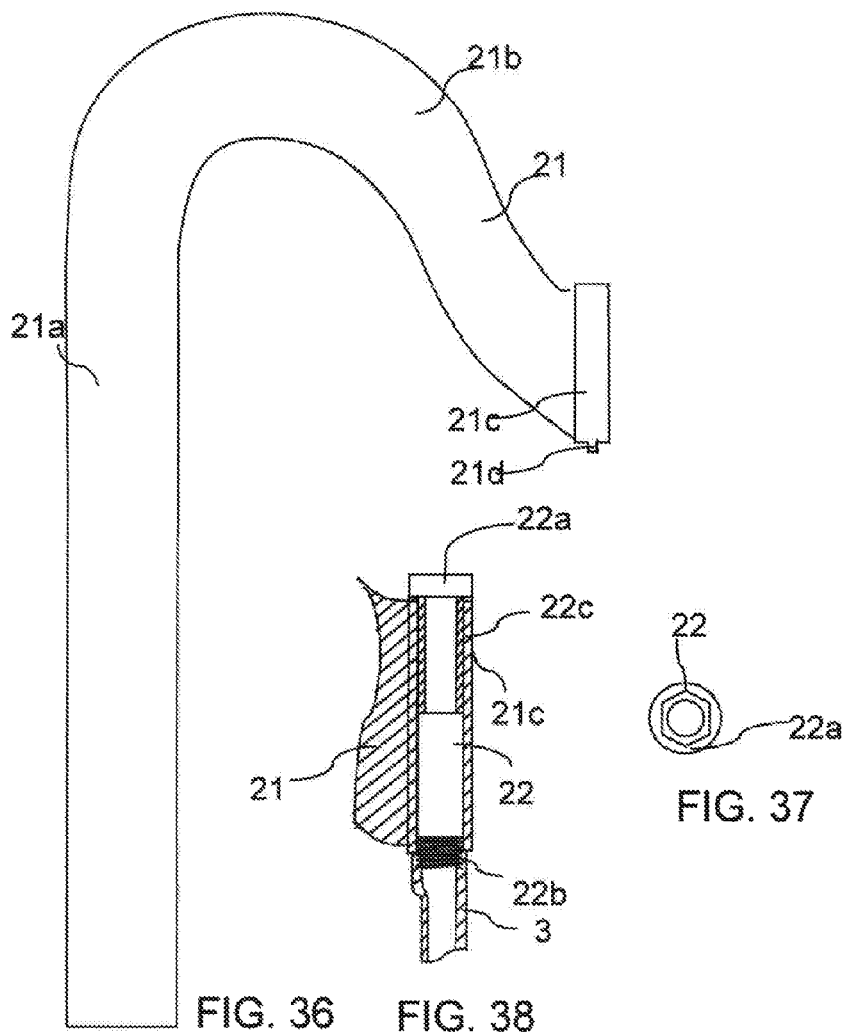
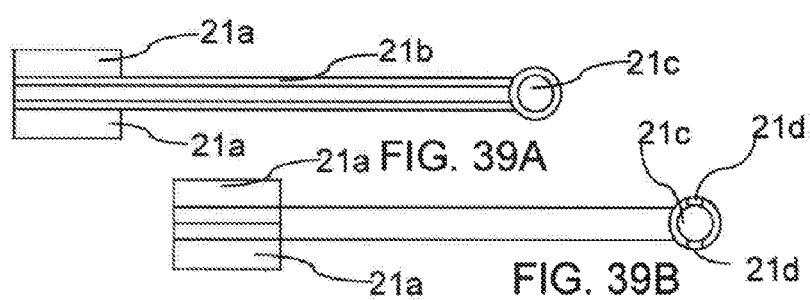

CEPHALOMEDULLARY NAILING SYSTEM OF VARIABLE ANGLE TO TREAT FEMUR FRACTURES AND THE UTENSILS USED TO PLACE THE SYSTEM

SUBJECT-MATTER OF THE INVENTION

The subject matter of this invention is a cephalomedullary nailing system of variable angle to treat femur fractures. The utensils used to place the system, including a valgus-producing osteotomy device, are also within the scope of this invention. The purpose for which this system is intended has innovative characteristics and advantages significantly enhancing the state of the art.

BACKGROUND OF THE INVENTION

The cephalomedullary nailing system of this invention contributes to solving three main problems: reduction of fractures (especially subtrochanteric fractures and inverted pertrochanteric fractures), improvement of assembly biomechanics to ensure favorable load axis for bony fragments and prevention of femoral neck collapse as well as offset and limb length loss, hence avoiding the possibility of reduced abductor power.

The types of proximal limb fractures affecting the femur are known as: femoral neck fractures, pertrochanteric fractures and subtrochanteric fractures.

As for femoral neck fractures: They affect the area between the trochanteric region and the femoral head. Femoral neck fractures are typically treated with partial-thread percutaneous cannulated screws placed perpendicularly to the fracture plane. This favors interfragmentary compression, which is beneficial for reduction and consolidation.

Pertrochanteric fractures affect the area between the greater and lesser trochanters, which represents the transition area between the femoral neck and the femoral diaphysis. The greater and lesser trochanters are insertion areas of the main gluteal region muscles: gluteus minimus and medius, iliopsoas and short rotators. Classical systems are comprised of the cephalomedullary nail (intramedullary nail with sliding screw) (intramedullary device) and plate-sliding screw (extramedullary device), in its different varieties.

Subtrochanteric fractures are located within the 5 cm of proximal femur segment immediately below the lesser trochanter. This type of fractures causes a typical proximal femur deformity in flexion, abduction and external rotation. Since these fractures affect mostly the subtrochanteric region and not the femoral neck, there is no point in discussing fixed length devices compared to adjustable length devices for the femoral neck. Extramedullary devices, instead of intramedullary devices, are an option for treating this type of fractures.

Within extramedullary devices, sheet-angled plate devices at 95° and the dynamic condylar screw are included. Intramedullary devices include ordinary anterograde intramedullary nails or cephalomedullary nails. Although fractures can be treated with ordinary intramedullary nails with transverse locking screws, it tends to be more suitable to use some type of cephalomedullary nail for femoral neck and head fixation.

Patent request EP2730243 is to do with an osteosynthesis device for treating femoral neck fractures. This includes a femoral nail with an oblong transverse section for insertion in the femur medullary cavity, as well as a cephalic screw for partial or full insertion in the femur neck and head. This cephalic femur has a transverse opening to house the femoral nail. The osteosynthesis device for treatment of femoral neck fractures is comprised of a femoral nail (1) with an oblong or rectangular transverse section for insertion in the medullary cavity, as well as a cephalic screw (2) for partial or full insertion into the femur head and neck. The cephalic screw (2) has a transverse opening (25) to house the femoral nail (1), which typically has a compression element (3) connecting the femoral nail and cephalic screw. Both opposite transverse walls, which are distal (252) and proximal (251) to the transverse opening (25), are inclined in the same direction in relation to the longitudinal axis (X1-X'1) of the traction bolt (2). Distance (D) between the stop edge (252a) of the distal transverse wall (252) located in the entry opening plane (253) of the transverse opening (25) and the orthogonal projection of the parallel edge (251b) of the proximal transverse wall (251) in the same entry opening plane (253) of the transverse opening (25) is higher or equal to the length (L) of the femoral nail (1). As a result, the femoral nail (1), cephalic screw (2) and compression screw (3) are designed to favor coupling of the cephalic screw (1) and the cephalic screw (2) by means of the compression element (3). This compression element is joined to the cephalic element (2), with pressure being applied to one lateral side (14, 15) of the femoral nail (1) so that the other lateral side (15, 14) of the femoral nail (1) comes in contact with the lower edge (251b) of the proximal transverse wall (251) of the transverse opening (25).

Patent request WO0156487 shows an orthopedic implant comprising: a hip screw, a sliding mechanism, an intramedullary nail and a compression screw. In the case of intraoperative static compression, this orthopedic implant provides dynamic post-surgery compression. It features the design of a hip screw implant, with an intramedullary nail which has a transverse section in any type of geometric shape and dimension. Transverse section shape and dimension can be the same or vary along the entire intramedullary nail.

Patent request EP 1072229 shows a synthesis element (10) for repair of femur fractures. This element has a femoral component that can be associated to the femur, as well as a cephalic screw which can be coupled to the femoral component at the femur head. A feature of the synthesis element is that the cephalic screw (11) can be initially joined to a first femoral component, comprising a stem (12) which can be inserted into a diaphysis channel in the femur. The other joint implies coupling a second femoral component comprising a plate (13) which can be laterally fixed to the outer femur side. Both joint options can be used alternatively to obtain at least two different synthesis element (10) configurations.

This invention is different to the previous state of the art in that it is based on the innovative geometry of the screw channel and the use of an additional locking screw. On the one hand, the nail can turn 360°, meaning it is simpler to introduce it through the screw. On the other hand, channel shape favors the nail being randomly locked based on the desired varus-valgus inclination (within an established varus-valgus inclination range). There are three support points counteracting varus/valgus forces, as well as rotational stabilization by means of the locking screws and slots (slotted version).

The fact that the nail support surface is homogeneous and has a circumferential section, gives the locking system more biomechanical stability and predictability.

The possibility of locking the nail to the screw at different angles is presented in two of the abovementioned patents. Having said that, their locking system is clearly insufficient.

An example is the description included in patent request EP 2730 243, which has a locking system in two clearly unstable support points due to the fact that there is no homogeneous nail support surface on the screw. As for patent request WO0156487, it presents a complex locking system by means of lateromedial compression with washers. This does not seem biomechanically stable because the nail needs to be drilled into the area more subjected to stress during limb placement, thus entailing a risk of implant rupture.

SUMMARY

FIG. 1 corresponds to a median sagittal section of the cephalic screw where FIG. 1A shows how the screw's transverse channel geometry is achieved; this geometry is obtained by removing from the screw volume the geometric shape, which corresponds to the volume forming inside a toroidal revolution surface; the central point of this surface coincides with the screw axis, which is inclined depending on the angle (variable). FIG. 1B shows this geometry could correspond to a double inverted, inclined and truncated cone from the screw volume; the distal surface (surface on which the nail is pushed during locking) of such truncated cone is modified (represented by the dotted line in the image) to ensure its sagittal section is circumferential and thus homogeneous to enable nail support on the screw.

Considering a large number of conventional nails failed in the cephalic screw ("cut" or "cut-out"), we think it is relevant to first place the cephalic screw on a proper location in the three space planes. This is so because in the case of conventional systems, screw introduction in the neck is conditioned by nail position.

Firstly, since this is a fixed length device with an interfragmentary compression system, fracture fixation includes the prevention of bone rupture in the trochanteric region and femoral neck fractures. This is different to existing cephalomedullary nails.

Furthermore, since work is done with a nail, it prevents the distal femur medialization failure which occurs in some fractures, when the lateral trochanteric cortex is affected because the nail itself becomes a mechanical obstacle.

Since the nail slides on a screw (of higher caliber), nail diameter is smaller than that of conventional nails, meaning abductor musculature aggression is reduced.

By having a smaller angle between screw and nail, there is higher bone thickness above the cephalic screw tip. This could theoretically reduce the risk of cut-out failure (upper femoral neck tearing caused by the screw).

An additional advantage is the cephalic screw accessory ("trochanteric support plate"), which may be useful in transverse ruptures when the greater trochanter tip is loose (it would be synthesized using screws locked to the plate and to the actual screw).

Since this is a non-sliding screw, cephalic screw protrusion to the lateral thigh side is prevented. Such protrusion tends to cause discomfort or even skin problems in patients who have undergone hip fracture surgery.

The screw placement angle facilitates putting such screw in a position higher than that of conventional nails, thus preventing contact with the fracture area. This is especially important in inverted pertrochanteric fractures, when the cephalic screw insertion point usually coincides with the fracture site.

Other nail advantages relate to valgus-producing osteotomy performance once the cephalic screw is placed (when the anatomical axis of the femoral neck is not adequate). Compared to the angled plate, this system is less complex and favors earlier loading (by being an intramedullary system) after valgus-producing osteotomy completion.

By means of the insertion-compression device and its extender-reducer, it is possible to manage the proximal fragment of the femur in the axial plane and the front-to-back plane.

By improving reduction possibilities through the principles of minimally invasive surgery, hip fracture recovery is more likely to be successful.

The cephalomedullary nail which is the subject-matter of this invention can be made of any material complying with existing regulations, as well as out of other materials suitable or useful for such purpose.

Based on all of the above, the cephalomedullary nailing system for femur fracture treatment of this invention, as well as the utensils used to place such system, provide this invention with innovative characteristics and advantages significantly enhancing the state of the art.

DESCRIPTION OF DRAWINGS

To complement the description provided and to favor better understanding of the features of this invention, a part of this descriptive report is comprised of a set of diagrams illustrating, but not limited to, the following things:

FIGS. 1-18 correspond to examples of the first version of the cephalomedullary nailing system, with a nail for trochanteric fossa insertion. More specifically, these figures show the following:

FIG. 1 corresponds to a median sagittal section of the cephalic screw.

FIG. 2 is a top view of the screw, whereas FIGS. 4 and 6 present the cephalic screw shown in FIG. 1 but seen from above and below.

FIG. 3 shows the axial section of the AB cut in FIG. 1.

FIG. 4 represents the upper (1e) and lower (1f) ellipses of the cephalic screw (1) channel (1d).

FIG. 6 represents the upper (1e) and lower (1f) ellipses of the cephalic screw (1) channel (1d).

FIG. 7 represents the left side or proximal part of the cephalic screw.

FIG. 8 shows the right side or distal part of the cephalic screw.

FIG. 9A represents a top view of the short proximal straight nail.

FIG. 9B represents a left view of the short proximal straight nail.

FIG. 9C represents a right view of the short proximal straight nail.

FIG. 10 shows a cut at the slot where stabilization screws rest (consolidating the screw-nail assembly). A top view of one of the stabilization screws is also included.

FIG. 11A is a top view of the distal locking screw, whereas

FIG. 15 is a cephalic screw composition including the short proximal straight nail, with two distal locking screws.

FIGS. 16 and 17 represent the angular range of nail movement on the lateral and front-to-back planes of the cephalic screw, respectively.

FIGS. 19-23 correspond to the second version of the cephalomedullary nail for insertion in the greater trochanter tip. More specifically, these figures show the following:

FIG. 19 is a median sagittal cut of the cephalomedullary nail's cephalic screw in its version for insertion in the greater trochanter tip.

FIG. 21 is top view of the short proximal angled nail, with two distal locking screws.

FIG. 22 corresponds to a sagittal cut of the same nail, with its two distal locking screws.

FIG. 24A shows a top view of the trochanteric support plate and flat head fixing bolt used to attach the plate to the cephalic screw. It also shows the trochanteric screws and their relation to the screw-nail system, as well as the orientation of the trochanteric screws locked to the plate.

FIG. 24B is a left side view of the trochanteric support plate adapted to the cephalic screw.

FIG. 24C is a left side view (from the proximal region) of the flat head fixing screw of the trochanteric plate.

FIG. 24D is a left side view (from the proximal region) of a trochanteric screw.

FIGS. 25-48 show the instrumentation required to place the cephalomedullary nail in its version for trochanteric fossa insertion. This also applies to the second version of the nail, with slight guidance system modifications. More specifically, this group of figures shows the following:

FIG. 26A is a top view of the protector for soft parts, with the needle reducer placed through the cephalic screw needle guide.

FIG. 26B is a left side view of the soft part protector.

FIG. 26C corresponds to the guide needle reducer top view (from the distal part).

FIG. 26D corresponds to the guide needle reducer left side view (from the distal part).

FIG. 26 E is a top view of the cephalic screw mill drilling the femoral neck through the guide needle.

FIG. 28 is a top view of the interfragmentary introduction-compression device, with the connector placed through it.

FIG. 29A is a top view of interfragmentary introduction-compression device connector 5.

FIG. 29B a view from the left side of such connector (from the proximal part).

FIG. 30 shows a sagittal cut of the connector presented in FIG. 29.

FIG. 31 is a perspective view from the proximal region of the introduction-compression device, together with the connector.

FIG. 32 is a top view of the extender-reducer device connected to the interfragmentary introduction-compression device.

FIG. 33 is a left side view of the extender-reducer device.

FIG. 34 is a sectional view, based on the AB cut shown in FIG. 32, at the level of the extender-reducer device with the introducer.

FIG. 35A is a left side of the 15 fixing bracket between the introduction-compression device and the extender-reducer device.

FIG. 35B is a top view of the 15 fixing bracket between the introduction-compression device and the extender-reducer device.

FIG. 36 is a top view of the needle locking guide.

FIG. 37 is a top view (from the proximal region) of the nail introduction guide connector screw.

FIG. 38 is a top view of the connector screw with a sagittal cut on the top half and its relation to the nail introduction guide, which is sagittaly sectioned.

FIG. 39A is a top view of the locking guide.

FIG. 39B is a bottom view of the locking guide.

FIG. 41 is a left side view of the nail introduction guide with the extender device placed on its central space.

FIG. 42 is a top view of the cephalomedullary nail, in a sagittal cut representing the introduction device connector through which the screwdriver is introduced to adjust stabilization screws. In turn, the distal locking guide and the drill bit for distal locking screws, are represented.

FIG. 47 corresponds to the AB cut presented in FIG. 45A.

FIG. 48 corresponds to the valgus-producing osteotomy device layout, placed on the trochanteric region where its stabilization is represented by means of needles.

DETAILED DESCRIPTION OF THE INVENTION

Figure 1:
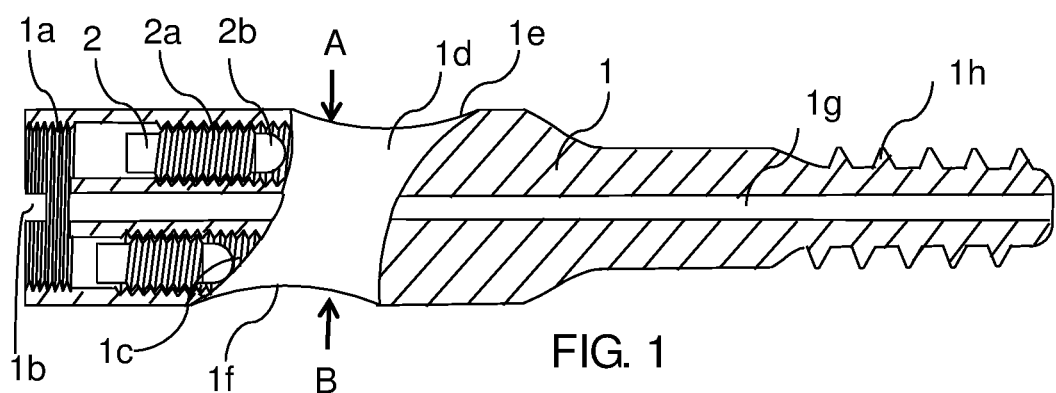

The cephalomedullary nailing system of this invention is basically different in that it is comprised of a cannulated screw, known as cephalic screw, which is introduced via the lateral side of the femur's trochanteric region. The cephalic screw trajectory aims towards the femoral head, through which an anterograde-shaped hollow nail is introduced in proximal femur limb (trochanteric fossa/greater trochanter tip).

This is a variable angle system with two possibilities: a trochanteric fossa insertion nail which is straight in its proximal part ("proximal straight nail") and a greater trochanter tip insertion nail which is curved in its proximal part ("proximal angled nail"). Both nails can be conformed with a single or multiple edges in its medial part of variable morphology, which would fit with a set of slots in the inner surface of the screw's transverse channel, doubling its rotational stability from a biomechanical point of view (on the one hand, rotational stability of stabilization screws on the nail's lateral slot and, on the other hand, of the edge/slot assembly created between the medial nail side on the cephalic screw transverse channel). The most suitable morphology for its implementation should be assessed by means of biomechanical analyses)

The cephalic screw channel through which the nail is inserted to run crosswise through the screw, has a configuration conceived to allow angular nail position variations, with a larger diameter in the nail's upper and lower parts and a smaller diameter in the central part. Geometrically speaking, the channel is equivalent to the volume that creates a toroidal revolution surface inside it (non-circumferential but elliptoid revolution). Another option is a channel with a double truncated cone shape and a lowered central surface in the screw part impacted by the nail during placement. Both geometric shapes are somewhat inclined in relation to the central axis of the cephalic screw. The reason for such inclination is to have a suitable angle favoring varus-valgus stabilization between the cephalic screw and the nail.

Both nail options include a locking system to consolidate the cephalic screw and the nail by means of stabilization screws. Furthermore, both types of nail can be locked distally by means of two screws, known as distal locking screws, which run through the lowest third of the nail. One of the screws can be placed dynamically, similarly to other options in the market.

With the cephalic screw it is also possible to place a plate with a screw locking system. This plate, known as trochanteric support plate, is coupled to the cephalic screw and favors the placement of trochanteric screws to fix the greater trochanter tip or increase femoral head/neck fixing when needed.

The nailing system is installed using specific instrumentation, which is a second point of interest of this invention. More specifically, once drilled to the femoral neck, the cephalic screw is introduced using a device which is fitted to the screw through a connector, enabling interfragmentary compression when fracture characteristics may require it. Such device, known as introduction-compression device, enables manipulation of the proximal femoral segment. To do that, there is a "T-shaped" extender device facilitating manipulation of the femur's proximal segment. This device, known as extender-reducer device, is connected to the introduction-compression device by means of a threaded bracket.

As for the nail, it is joined to an arch-shaped guide, known as nail introduction guide, by means of a connector screw. This guide enables nail insertion to drive nail insertion, as well as having the extender-reducer device run through to facilitate stabilization screw tightening. This is possible thanks to the "tuning fork-shaped" morphology of its vertical arm. Furthermore, this guide enables drilling and subsequent introduction of distal locking screws by using a distal locking guide.

When medullary cavity drilling is required, this invention also foresees the use in nails of special drills capable of gradually perforating the screw channel.

The invention foresees the use of a valgus-producing osteotomy device in cases of angular femoral neck axis alteration. Such device can be placed and used to perform a wedge resection of the intertrochanteric region once the cephalic screw is placed. As a result, proper femur's cephalic angle recovery can be ensured by manipulating its proximal fragment with the placement instrumentation.

This specific screw channel geometry and additional locking screw placement of this invention present a number of innovative, differential features. On the one hand, the nail can turn 360°, meaning it is simpler to introduce through the screw. On the other hand, channel shape favors the nail being randomly locked based on the target varus-valgus inclination (within an established varus-valgus inclination range). There are three support points counteracting varus-valgus forces, as well as rotational stabilization by means of the locking screws and slots (slotted version).

The fact that the nail support surface is homogeneous and has a circumferential section, gives the locking system more biomechanical stability and predictability.

The following is a description of the first development mode of the cephalomedullary nailing system of this invention, in which the nail (3) is straight in its proximal region to facilitate insertion through the trochanteric fossa.

In this option, the invention set is comprised of a cephalic screw (1), a nail (3) which can short or long, as well as one or two locking screws (4). There is also the option of using a trochanteric support plate (9) with trochanteric screws (11).

The cephalic screw (1) for the proximal straight nail (3) is transversally cannulated (1d) and has an asymmetric diameter, meaning it needs to be assessed through biomechanical analyses. Geometrically speaking, the screw's channel (1d) is obtained by removing from the screw volume the geometric shape, which corresponds to the volume (1j) that forms inside a toroidal revolution surface. The central point of this surface coincides with the screw axis, which is inclined depending on the angle (variable). The toroidal revolution surface is obtained by turning a circumference (generating curve) around the rotation axis, which does not intersect with it in any point (FIG. 1A). Considering varus-valgus screw inclination is greater than front-to-back inclination, such turning is not circumferential but elliptical. It has an elliptical section in the coronal plane. In the proximal and distal parts of the channel, such geometric shape is modified to increase the screw's mechanical resistance, which then has a rectilinear section. The central axis (circumference rotation axis) has a strong inclination determined by the angle between the vertical axis and the rotation axis of the circumference defining the toroidal revolution. Considering the nail (3) goes through the channel (1d), this geometric shape allows for a 360° nail (3) inclination, with varus/valgus inclination limits of 15° (angular varus-valgus inclination range of 30°) and front and back inclination of 10° (angular front-to-back inclination range of 20°). That means an angular range of +/−15° for varus-valgus inclination and of +/−10° for front-to-back inclination. The bisecting angular inclination range corresponds to the circumference rotation axis which, when turning, defines such volume.

Figure 1A:
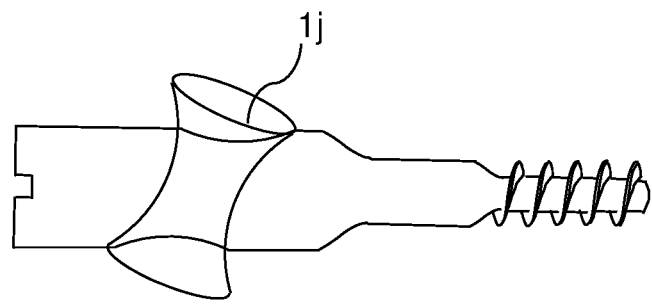
FIG. 1A shows how the screw's transverse channel geometry is achieved. This geometry is obtained by removing from the screw volume the geometric shape, which corresponds to the volume forming inside a toroidal revolution surface. The central point of this surface coincides with the screw axis, which is inclined depending on the angle (variable). Alternatively, this geometry could correspond to a double inverted, inclined and truncated cone (1B) from the screw volume. The distal surface (surface on which the nail is pushed during locking) of such truncated cone is modified (represented by the dotted line in the image) to ensure its sagittal section is circumferential and thus homogeneous to enable nail support on the screw.

The medial sagittal cut of the cephalic screw (1) shown in FIG. 1, features the transverse channel (1d) for the nail (3). It is a longitudinal cannulated (1g) screw with short distal thread (1h). It also has two notches (1b) in diametrically opposed positions of its proximal part to stabilize the guide-screw connection by tightening in the inner thread (1a) of the proximal part (1b). Furthermore, it includes two precharged stabilization screws (2) with thread (2a) to favor movement through two threaded tunnels (1c) of the cephalic screw into the target position (after fracture reduction). FIGS. 1, 2, 4 and 6 represent the upper (1e) and lower (1f) ellipses of the cephalic screw (1) channel (1d).

Considering that a straight nail (3) cannot further incline from the midpoint of the angular inclination area sides, that bend section can be straightened by modifying the proximal and distal part of the screw (1) channel (1d) in order to increase the biomechanical strength of the screw (1).

Figure 1B:
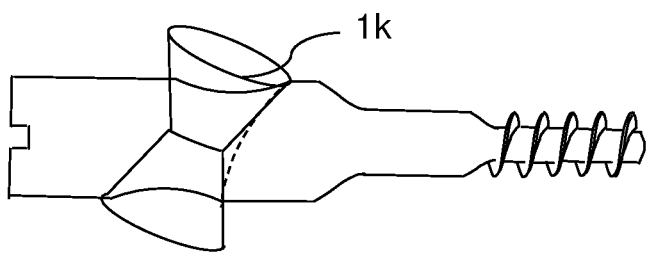
Figure 2:
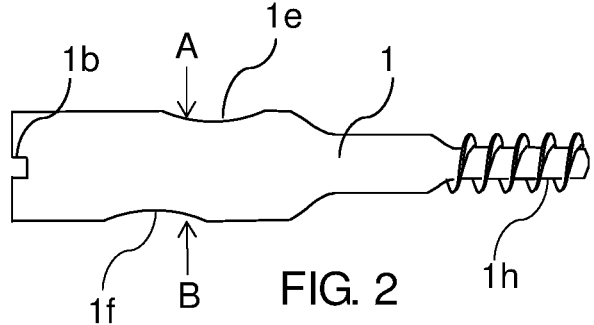
Figure 3:
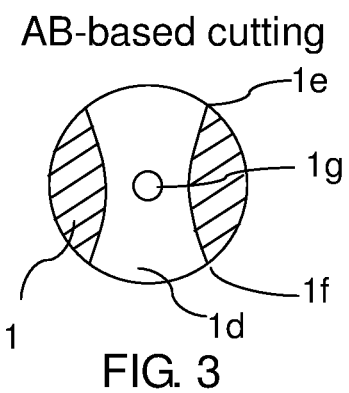
Figure 4:
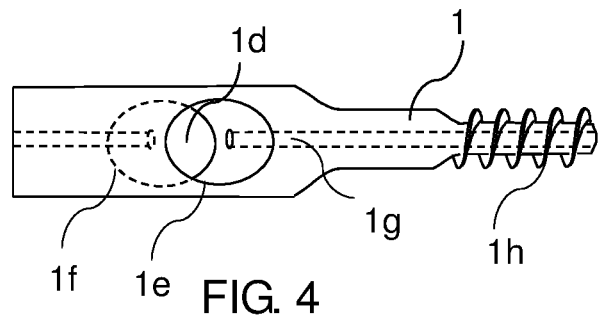
Figures 5A, 5B:
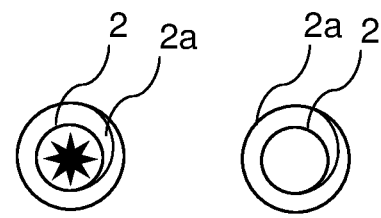
FIG. 5A corresponds to a side view from the left stabilization screw.
FIG. 5B corresponds to a side view from the right stabilization screw.
Figure 6:
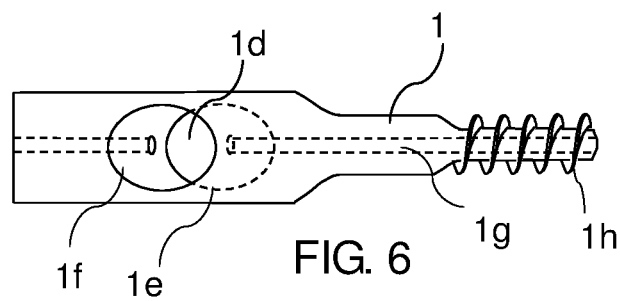
Figure 7:
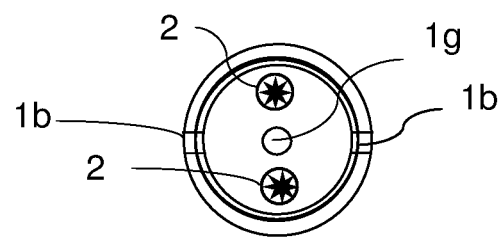
Figure 8:
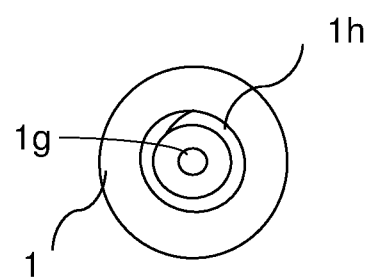

Alternatively, the screw can be manufactured using a transverse channel obtained by subtracting from the screw volume the volume of an inverted double truncated cone (1k), the center of which coincides with the screw axis, which is inclined. In this case, the distal part on which the nail rests is modified, making its sagittal section circumferential without affecting the range of nail inclination on the screw (FIG. 1B).

Similarly, the slotted screw variant (FIG. 13) can have a number of rectilinear vertical striations (edges) (3h) which would fit in the longitudinal grooves of the screw surface on which the nail rests (slots) (1i). The edges can have a different section (rectangular, triangular or circumferential) and be single or multiple (FIGS. 13F through 13K).

Figure 9:
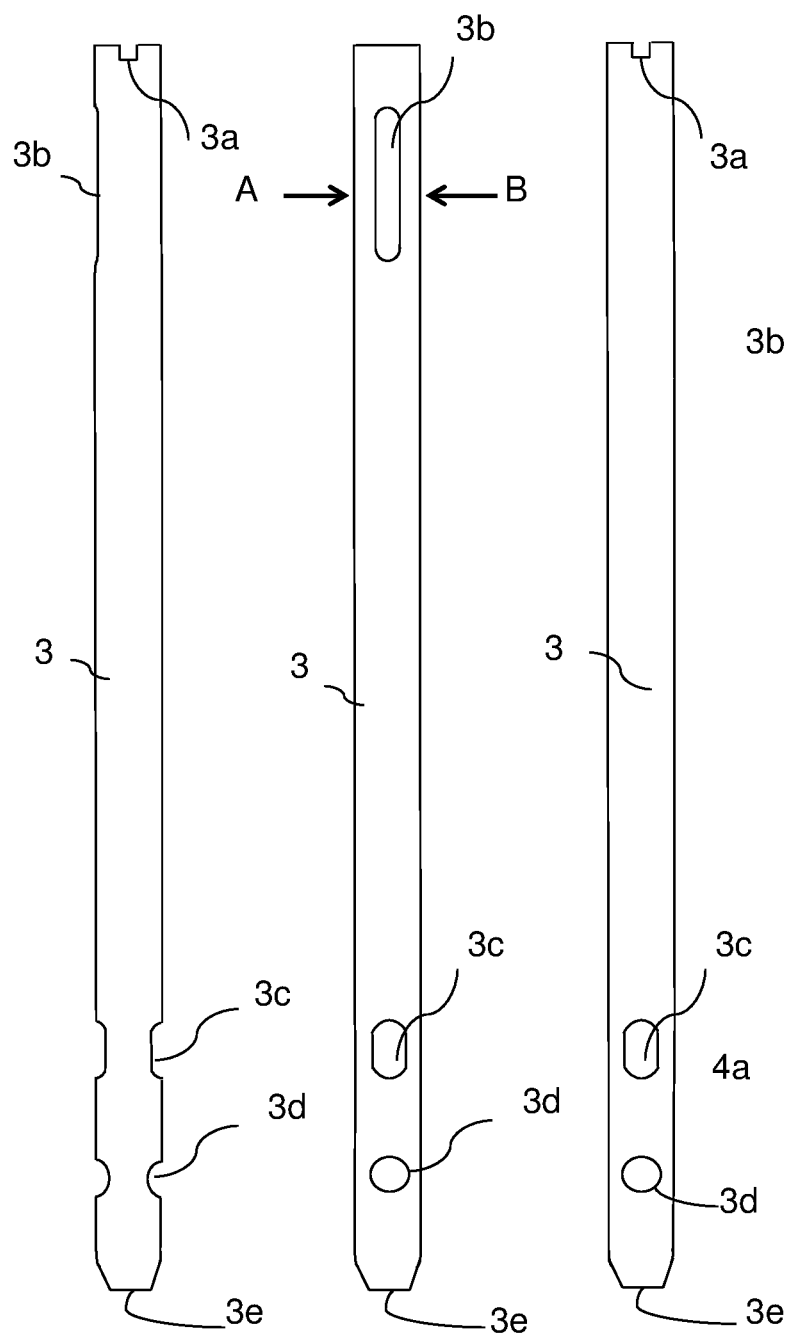
Figure 10:
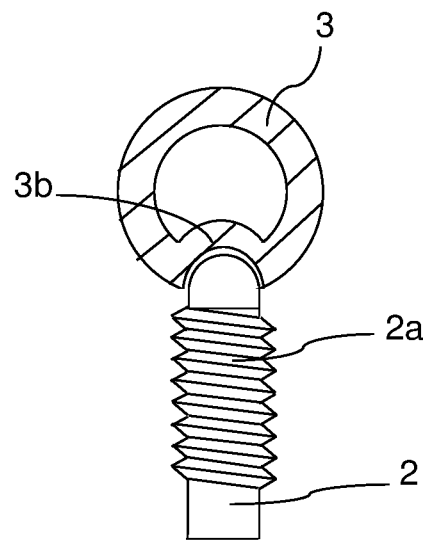
Figure 14A:
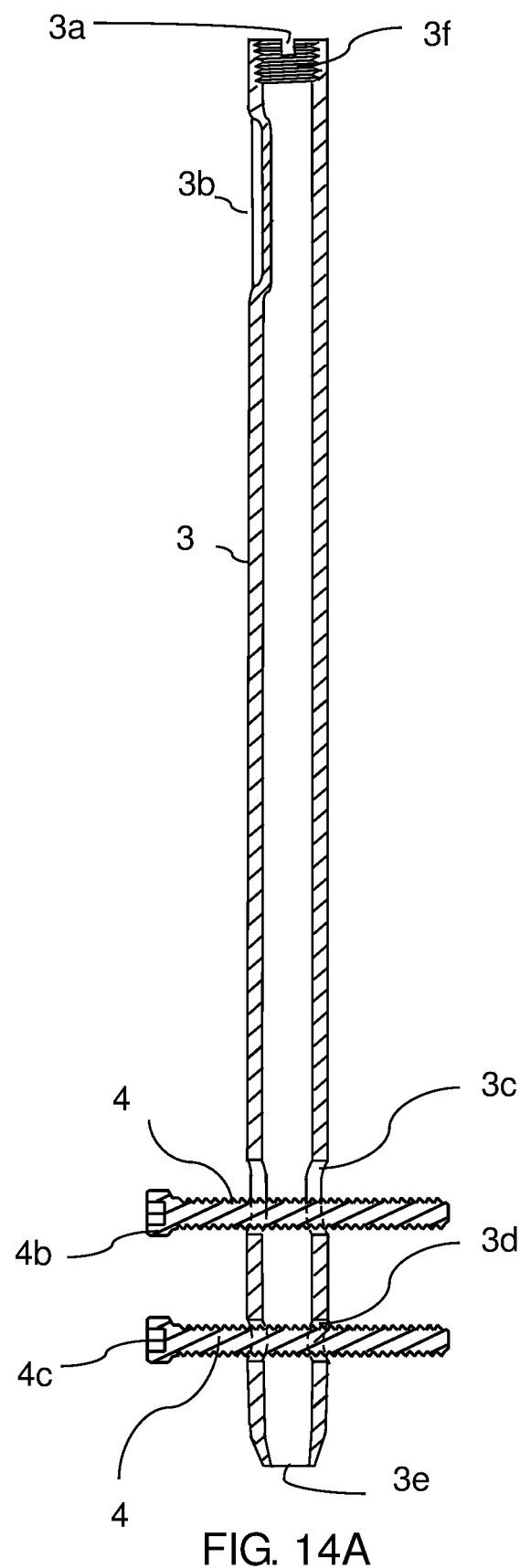
FIG. 14A is a median sagittal cut of the short "proximal straight nail", with two distal locking screws.
Figure 14B:
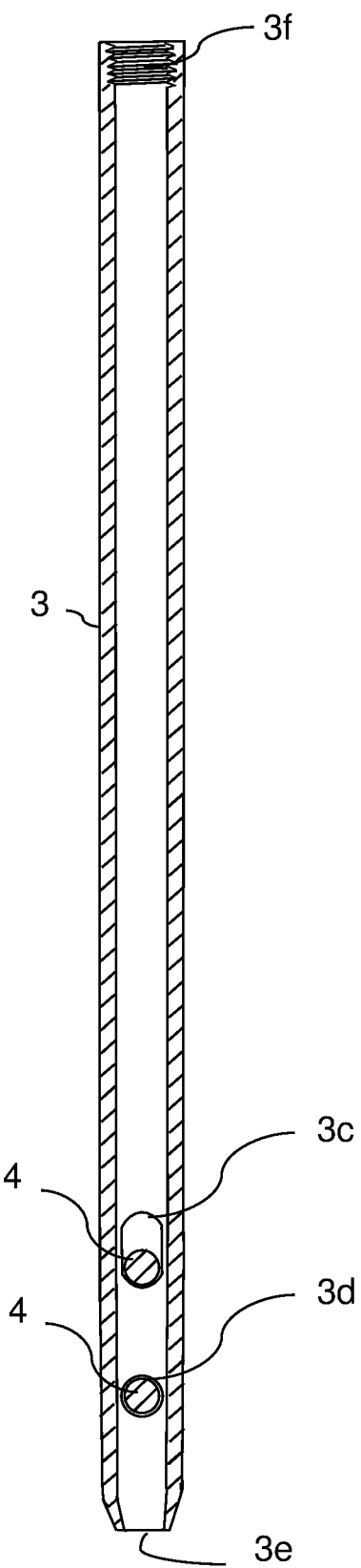
FIG. 14B corresponds to the coronal cut of the same nail.
Figure 15:
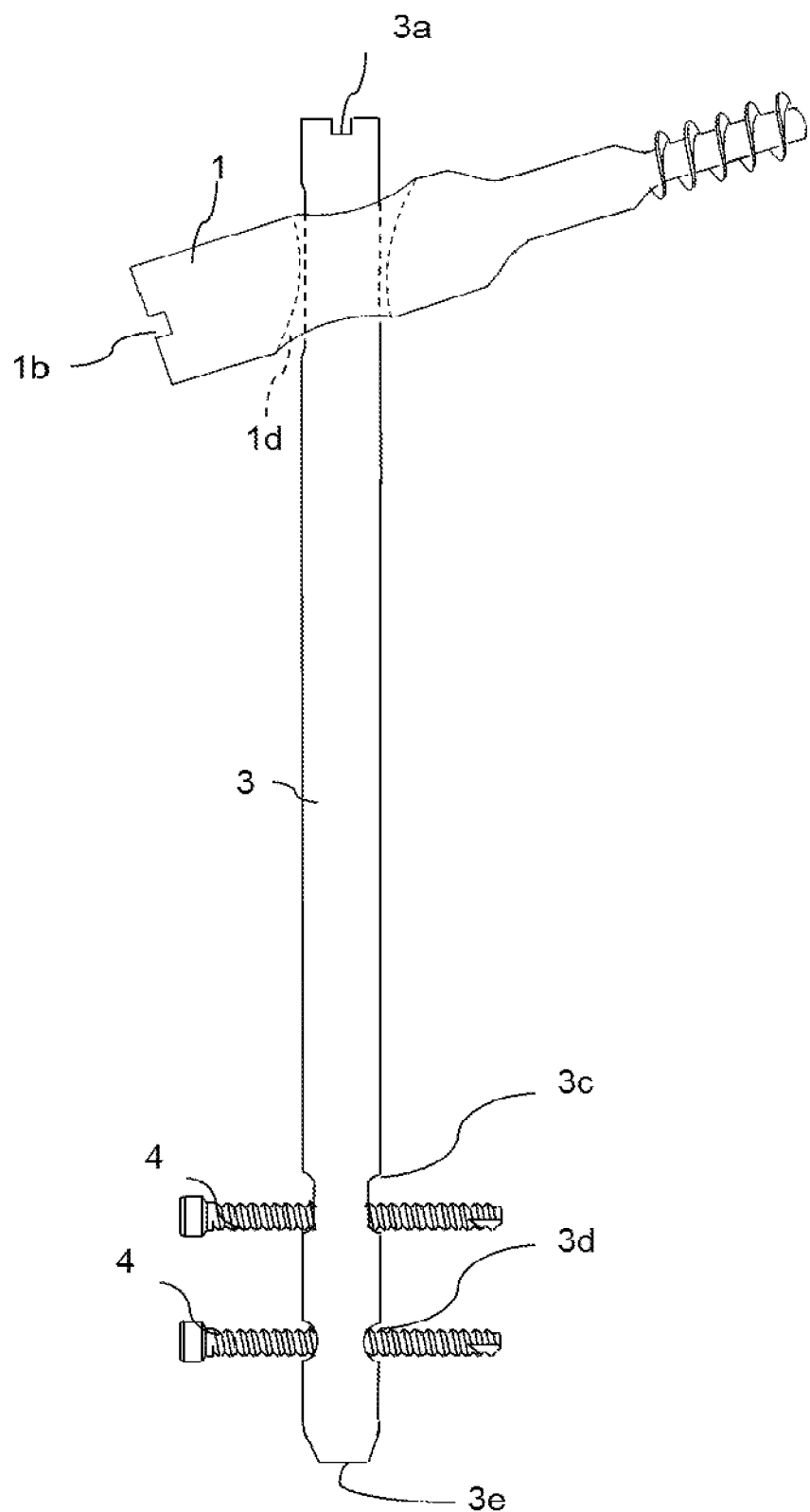

As for the proximal straight variant of the nail (3), it is a guided (could be milled) cannulated nail of different diameters. It has a longitudinal groove (3b) similar to a channel on the side of its upper region, where stabilization screws (2) rest. These stabilization screws are inside the cephalic screw (1) (FIGS. 9B, 10, 12 and 14a). It also has perforations in the distal part, one oval-shaped in the upper part (3c) and one circumferential (3d) in the lower part, with the aim to house distal locking screws (4) when needed (FIGS. 9 and 14). The proximal part has two notches (3a) to increase connection stability with the locking guide (16) and proximal thread (3f). It has a central inner channel (3e) across its entire length and a slotted version used with an edged nail as initially described.

Figure 17:
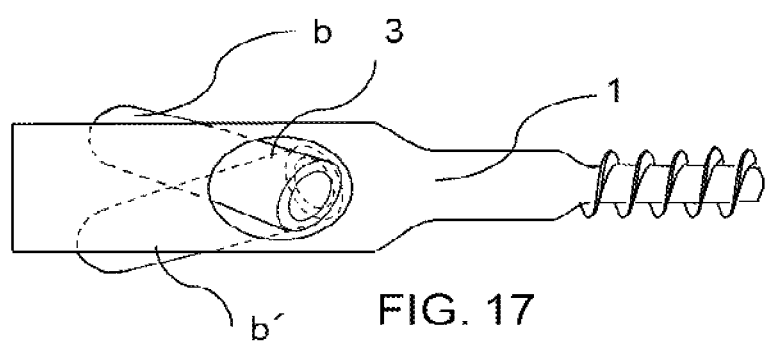
Figure 18A:
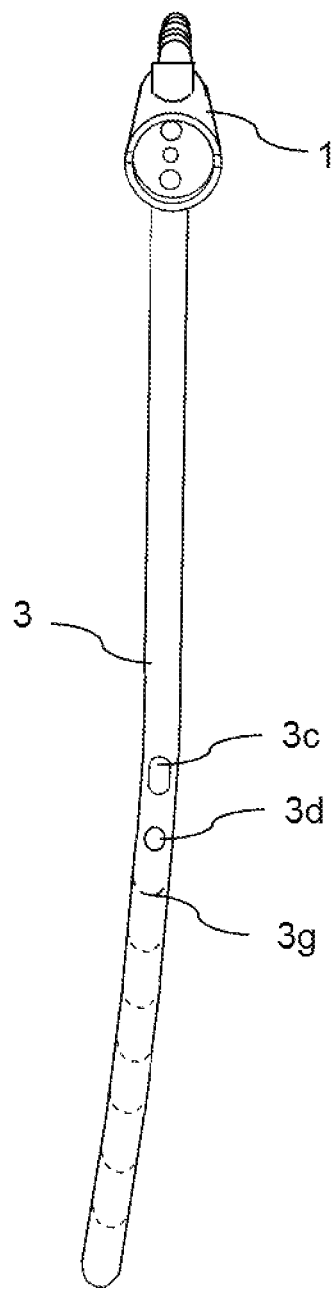
FIG. 18A shows the assembly comprised of the long proximal straight nail and the left side of the cephalic screw.
Figure 18B:
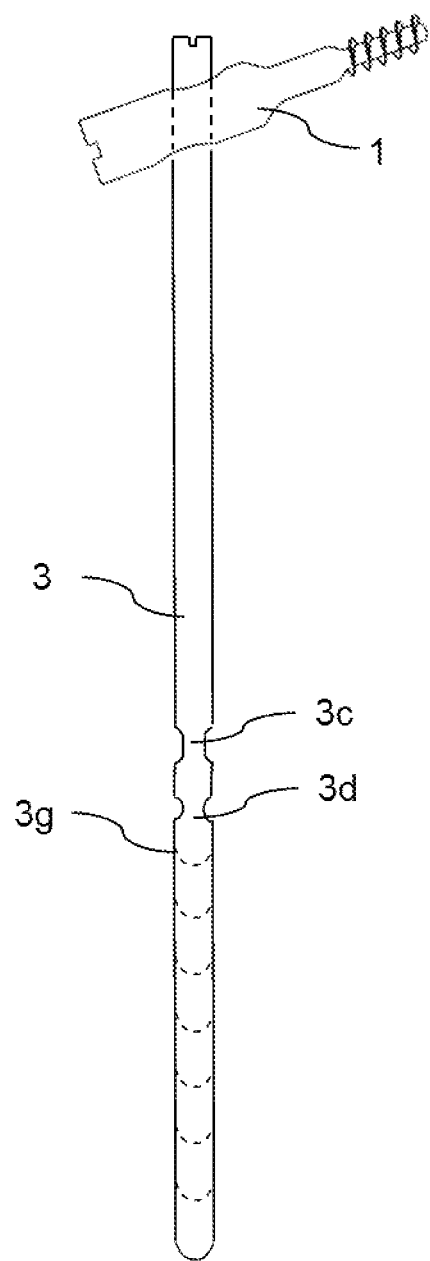
FIG. 18B shows an upper view of the same thing.

The nail (3) can be short (FIGS. 9 through 17) or long, as shown in FIGS. 18A and B. The long nail (3) is anatomic, that is, curved in its distal part similarly to the front bend of the femur. Thus, some nails (3) are used for the right side and other nails (3) for the left side. The nail has a variety of lengths represented with a dashed line (3g) in order to adjust to femurs of different length. In such case, it is recommended to mill the femoral channel using special mills prior to placing the nail.

Figure 16:
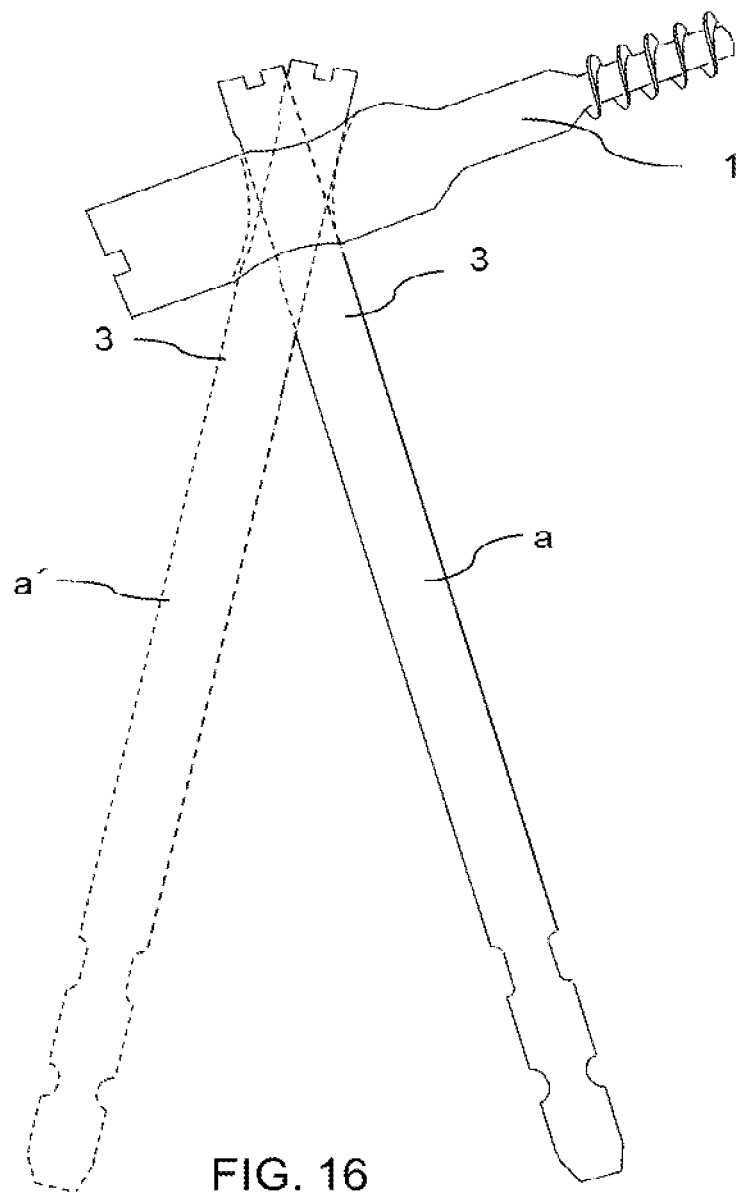

The angular varus-valgus inclination range is schematically represented in FIG. 16 ("a" maximum varus inclination, "a" maximum valgus inclination), whereas the front-to-back inclination range is presented in FIG. 17 ("b" maximum front inclination, "b" maximum back inclination).

Due to the design of the cephalic screw (1), once it is placed in the femoral neck, it could provide 15° of additional valgus in relation to the proposed standard angulation of 115°. Thus, it is possible to place the screw (1), perform the lateral subtraction valgus-producing osteotomy and force the valgus to reduce the femur before or after placing the nail (3). Considering screw (1) design is limited to 15° of valgus from the standard position, in case further valgus correction was needed the screw could be placed slightly in varus (up to a maximum of 30° of valgus by placing the screw at 100° of varus).

Figure 11A:
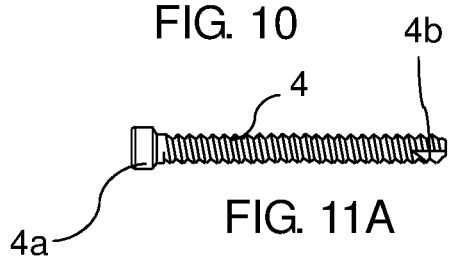
Figure 11B:
FIG. 11B shows the left side of the screw.
Figures 12A, 12B:
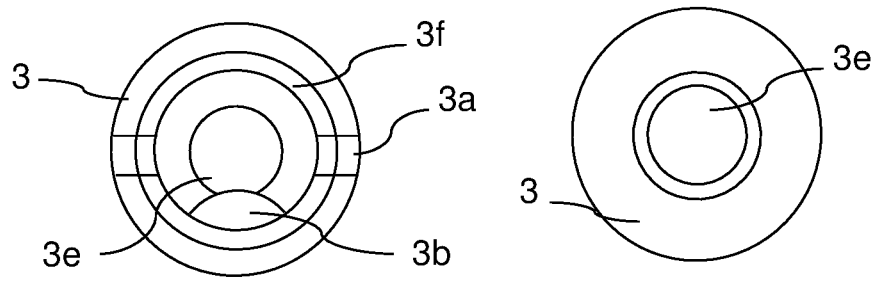
FIG. 12A is a top view (proximal nail end) and FIG. 12B is a bottom view (distal nail view).
Figure 13A:
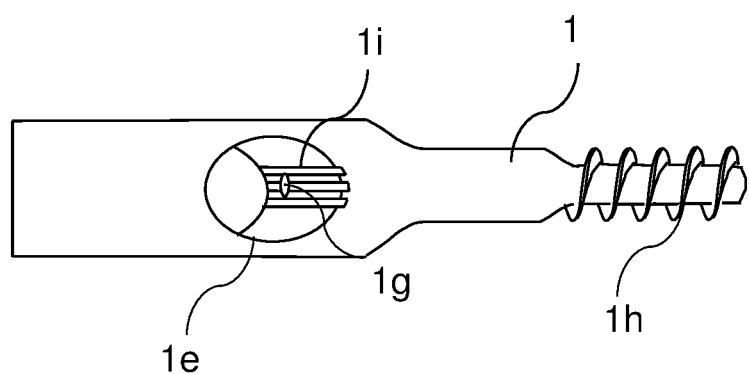
FIG. 13A is a top view of the cephalic screw's slotted version.
Figure 13B:
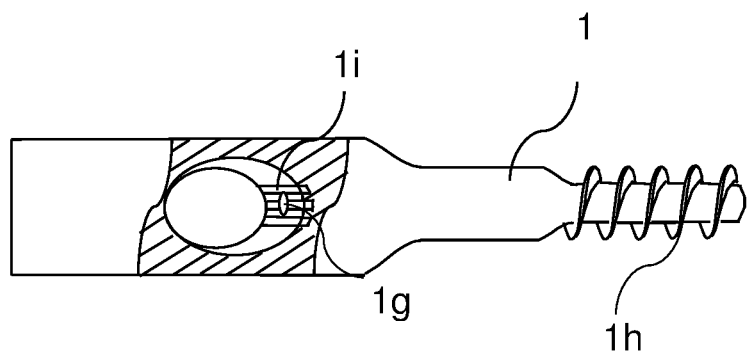
FIG. 13B is a top view of the cephalic screw's slotted version with a longitudinal front-to-back cut in its upper part.
Figures 13C, 13D:
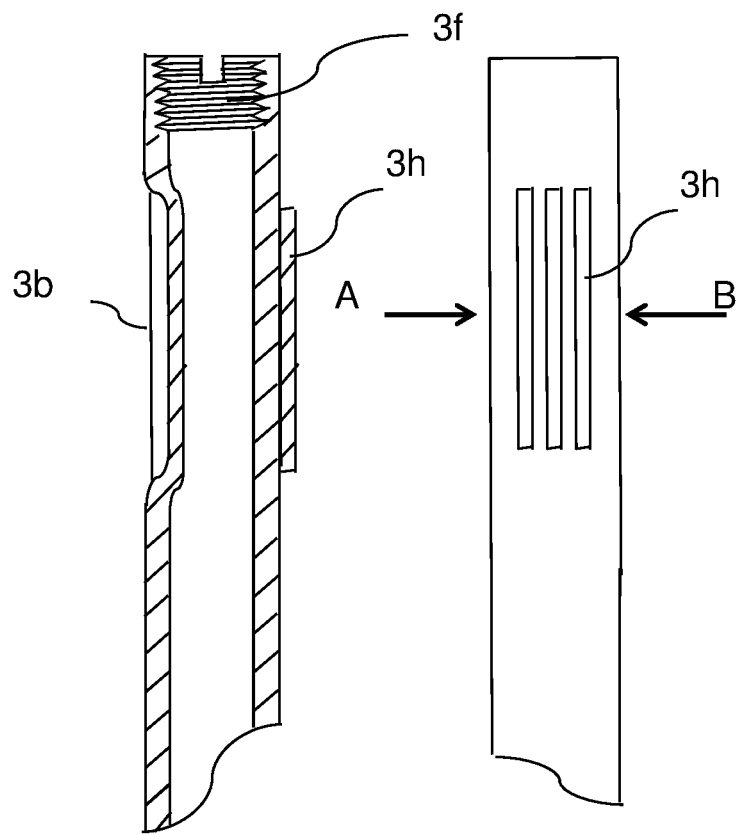
FIG. 13C is a sagittal cut of the nail's slotted version (proximal nail part).
FIG. 13D shows the left side of the slotted nail.
Figure 13E:
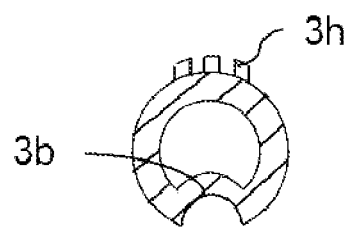
FIG. 13E is a transverse cut of the nail's slotted version (AB cut of FIG. 13D).
Figure 13F:
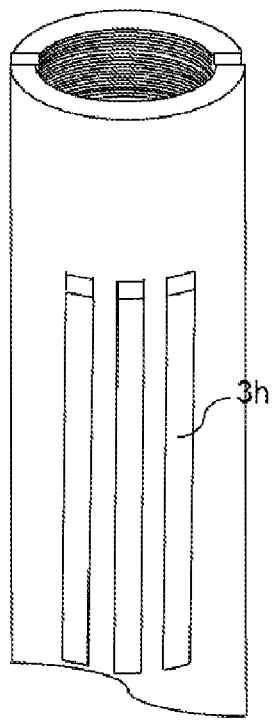
FIG. 13F corresponds to a perspective view of the upper nail pares version with square cross edges.
Figure 13G:
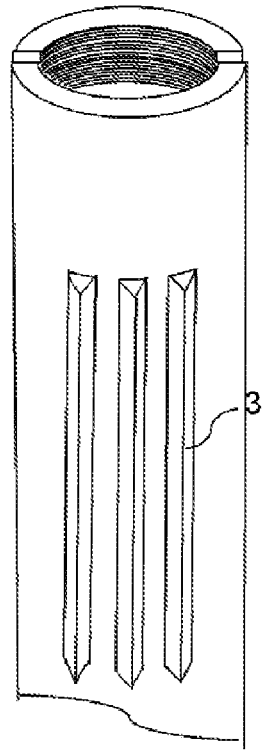
FIG. 13G corresponds to a perspective view of the upper nail part's version with triangular edges.
Figure 13H:
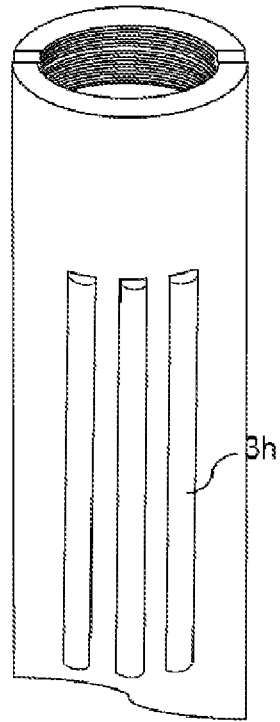
FIG. 13H corresponds to a perspective view of the upper nail part's version with semicircular edges.
Figure 13I:
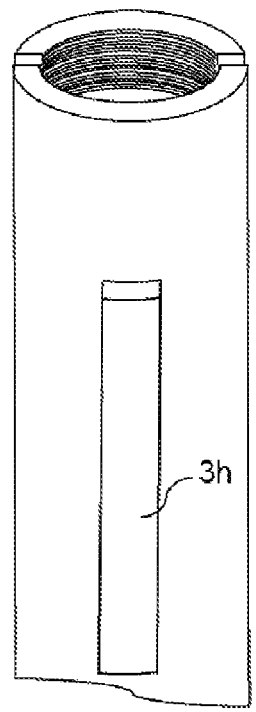
FIG. 13I corresponds to a perspective view of the upper nail part's version with a single square cross edge.
Figure 13J:
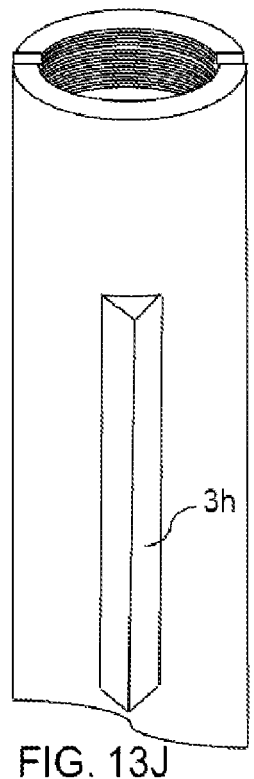
FIG. 13J corresponds to a perspective view of the upper nail pares version with a single triangular edge.
Figure 13K:
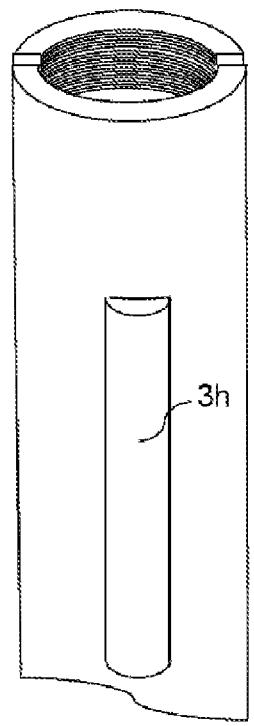
FIG. 13K corresponds to a perspective view of the upper nail pares version with a single semicircular edge.

Locking screws (4) are conventional cortical screws, similar to other existing state-of-the-art locking screws for femoral nails. They have a head (4a) with an inner hexagonal cavity (4c) suitable for screwdrivers of similar morphology. They also have a small notch (4b) in their distal part to make them self-tapping (FIGS. 11A & 14).

The cephalic screw (1) is compatible with an accessory to be placed in its proximal part, a trochanteric support plate (9) consolidated with the same cephalic screw (1). This consolidation is achieved by means of a flat head fixing screw (10) of proximal head (10a) and a large hexagonal cavity (10b) for a large hexagonal screwdriver. It also has a distal thread (10c) and protruding edges (9c) which fit into the notches (1b) of the proximal screw part (1). The support plate (9) facilitates locking trochanteric screws (11) into the plate to fix the greater trochanter when there is fracture comminution or even pointing them towards the femur neck-head. Trochanteric screws (11) are connected to the trochanteric support plate (9) by means of four threaded orifices (9a). It also has drill holes (9b) to run suture thread through them in case some bone fragment (osteosuture) (FIGS. 24A-D) needs to be fixed.

In the second development variant of the cephalomedullary nailing system of this invention, the nail (3) is angled in its proximal area for greater trochanter tip insertion. It comprises the following:

A cephalic screw (1), a proximal curved nail (3) (short or long) which can short or long, as well as one or two locking screws (4). As in the previous variant, there is the option of having the nail (3) use a trochanteric support plate (9).

Figure 19:
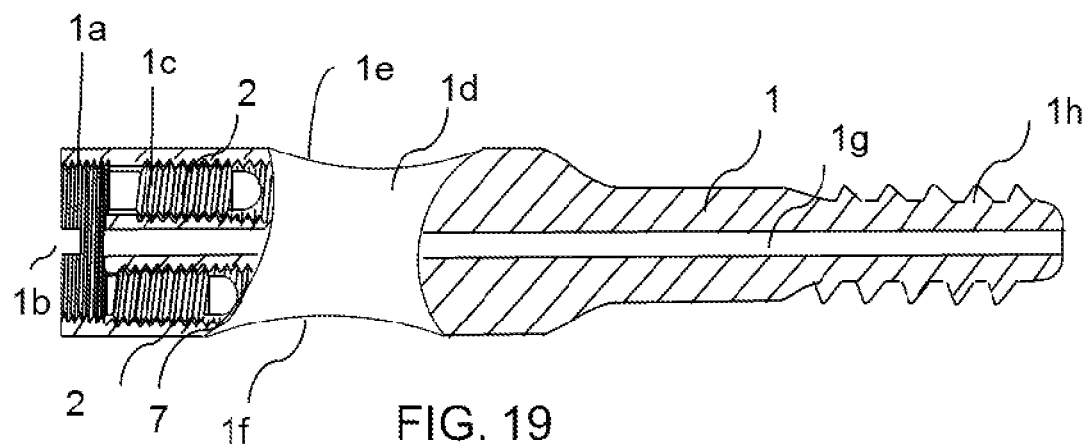
Figure 20A:
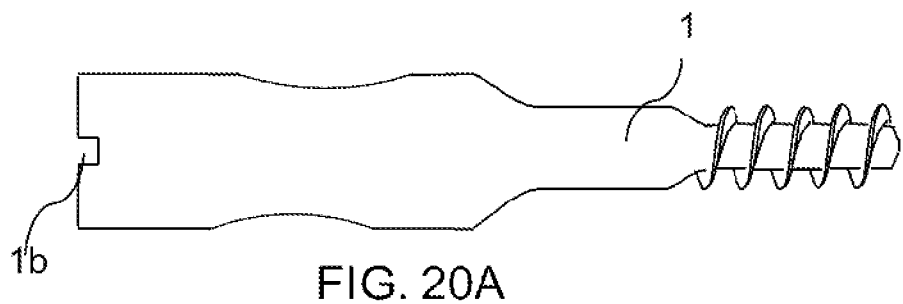
FIG. 20A is a top view of the same screw.
Figure 20B:
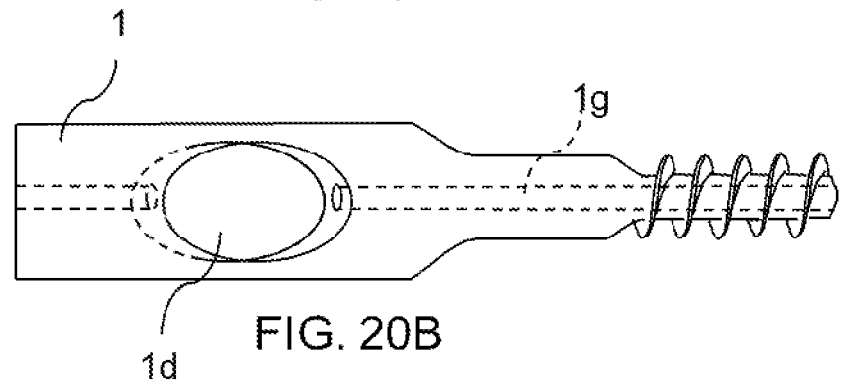
FIG. 20B presents the cephalic screw shown in FIG. 10 (prior 19 & 20) but seen from above.
Figure 20C:
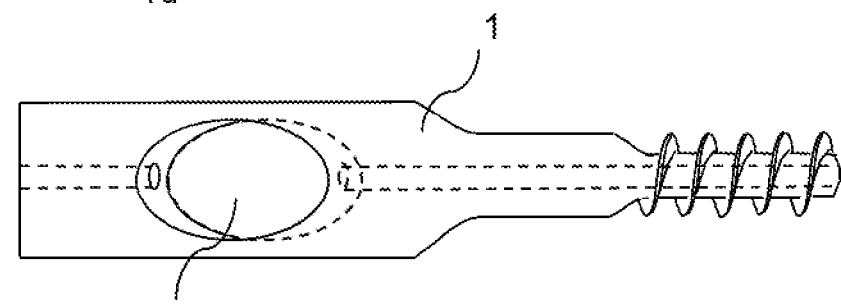
FIG. 20C presents the cephalic screw shown in FIG. 10 (prior 19 & 20) but seen from below.
Figure 21:
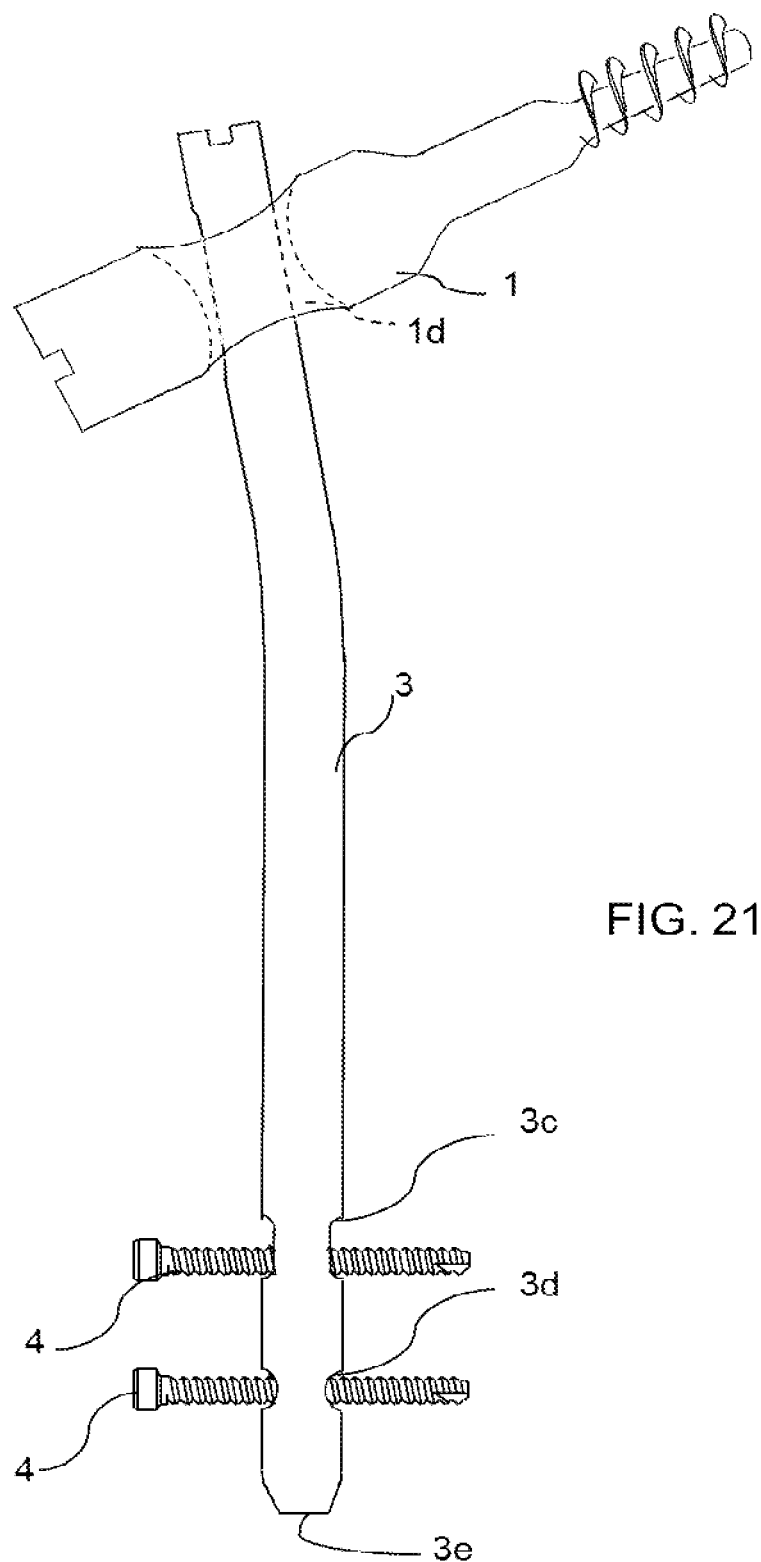
Figure 22:
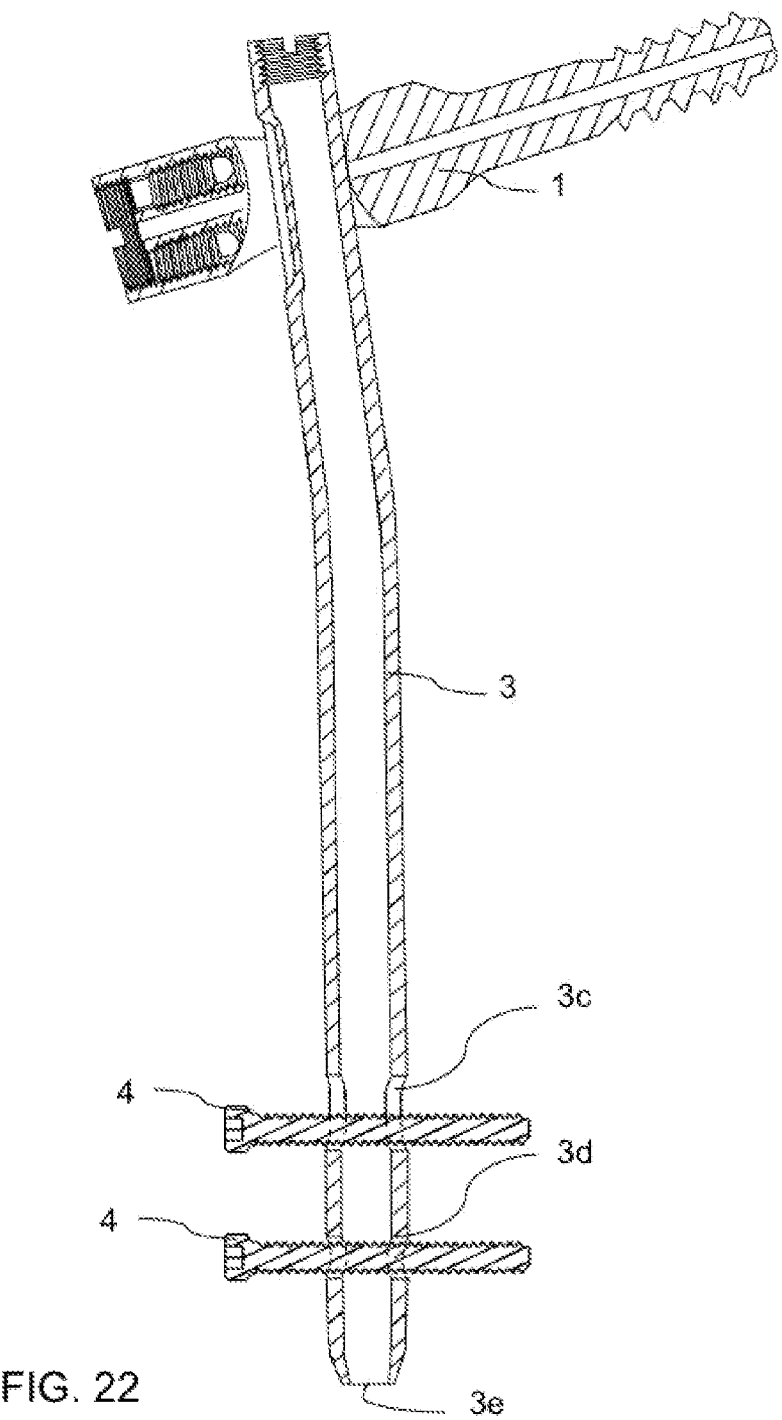

The cephalic screw (1) in this option is similar to the previous one. However, in this option the nail is introduced from a lateral position in relation to the femoral channel, not from a central position as it occurred with the nail for trochanteric fossa insertion. As a result, the inclination varus angle of the nail (3) on the screw (1) increases to facilitate nail insertion. To do that, the screw (1) channel (1d) is more lateralized (FIGS. 19 and 20). Inclination limits towards varus/valgus are 30° (angular varus-valgus inclination range of 60°), whereas the front and back inclination is 10° (angular front-to-back inclination range of 20°). Since the nail has a proximal bend of 10°, the resulting angle between the cephalic screw (1) and the distal part (3) of the nail would be 125°.

Figure 23A:
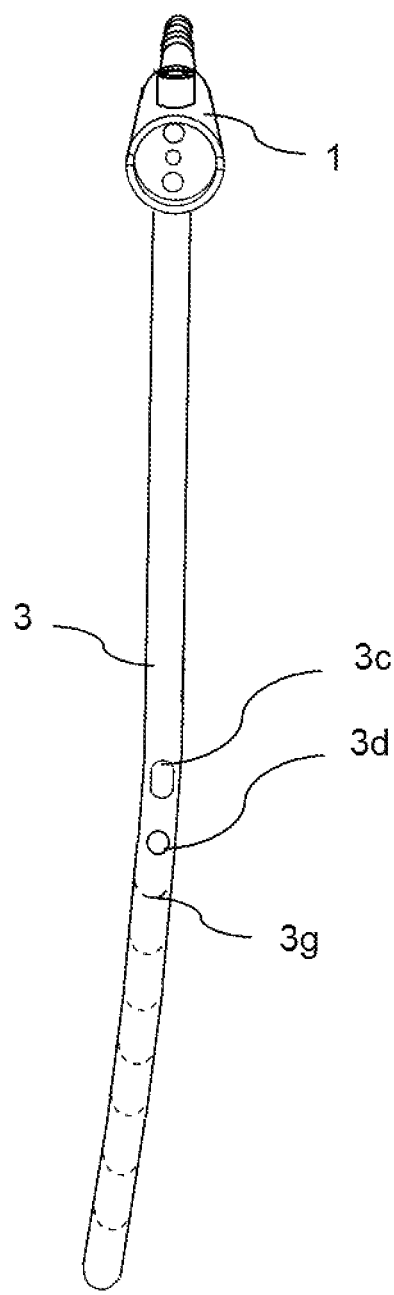
FIG. 23A shows the assembly comprised of the long proximal angled nail and the left side of the cephalic screw.
Figure 23B:
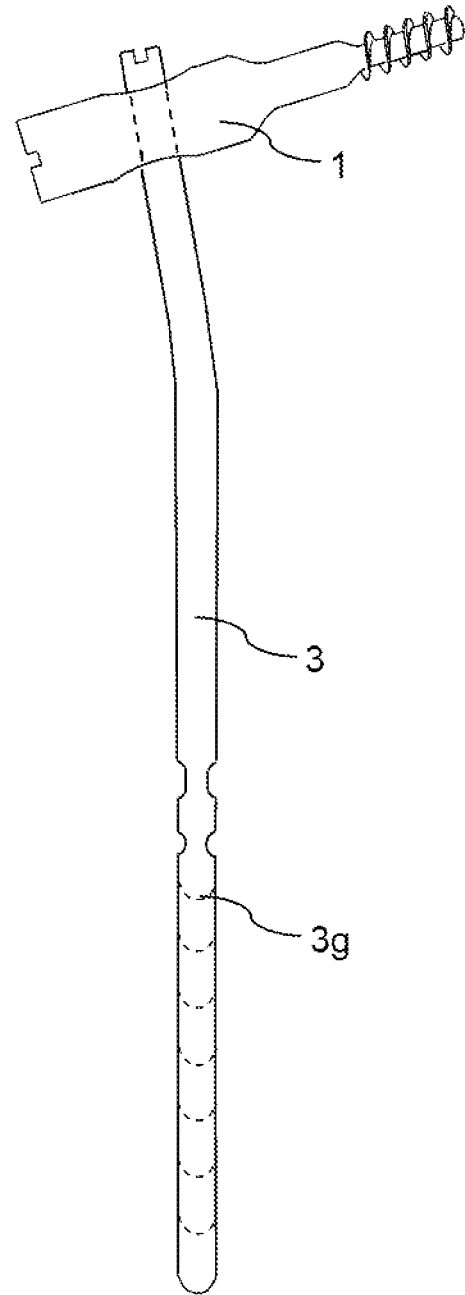
FIG. 23B shows an upper view of the same thing.
Figures 25A, 25B:
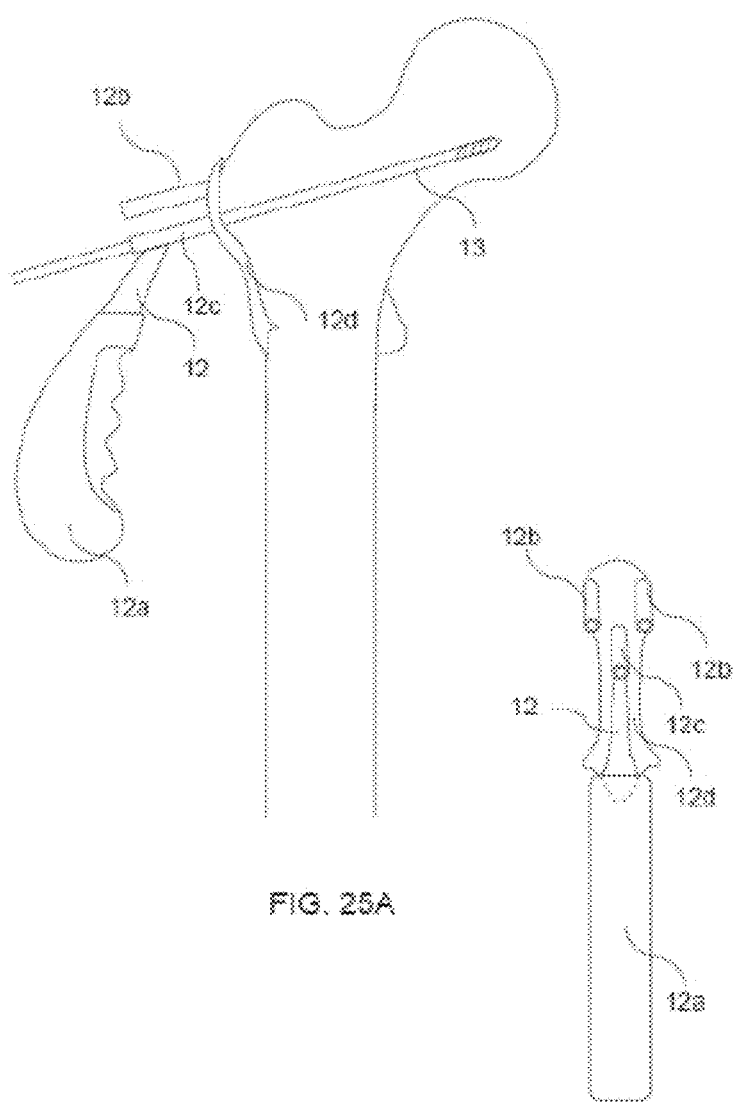
FIG. 25A is a top view of the needle placement guide through which the cephalic screw is placed.
FIG. 25B is a left side view of the needle placement guide.

As for the proximal curved nail (3), it is generally similar to the proximal straight nail (3), although in this case the nail has a proximal part angulation of 10° to adapt to the proximal femur morphology. It can be short or long. The long nail (3) is anatomic, with a front convexity bend to adapt to the femoral diaphysis morphology (FIG. 23A). It has various lengths (3g) so as to adapt to specific femur types or fracture characteristics. As they are anatomic, long nails (3) are divided depending on whether they are to be used on the right or left side.

Lastly, locking screws (4) are also similar to those of the previous variant.

FIGS. 25 through 48 show specific instrumentation also associated to this invention and used to place the advocated cephalomedullary nailing system. To facilitate understanding of the elements comprised within this instrumentation, figures only show the proximal straight variant of nail (3) instrumentation used for trochanteric fossa insertion. As for the proximal curved nail (3) variant for greater trochanter tip insertion, the instrumentation is similar with slight variations resulting from proximal nail (3) angulation.

More specifically, this instrumentation includes a femoral neck (12) guide needle which is manipulated by means of a handle (12a) and has a bone support surface (12d) resembling femur anatomy. It also has two upper tubular guides (12b) for anti-rotating guide needles (13) and a lower tubular guide (12c) for a cephalic screw guide needle (13), a soft part protector (14) with a handle (14a) and a tubular element with a distal limb equipped with stabilization gears (14c), as well as a needle reducer (15) which is cannulated (15a) to allow the guide needle to run through it. It also has a cephalic screw drill bit (16) and a medullary cavity milling system with a specific morphology terminal ("special mills") (17) to mill the medullary femur cavity. Furthermore, it has an interfragmentary introduction-compression device (18) with a connector (19) and an extender-reducer device (20) to position the cephalic screw (1), an introduction guide (21) for the nail (3) and a locking guide (27) for distal locking screws (4).

Since nail insertion requires milling the medullary cavity (usually 1.5 mm more than nail diameter) to adjust it to cephalic screw (1) cavity caliber (1d), special mills (17) are to be used.

Figure 27A:
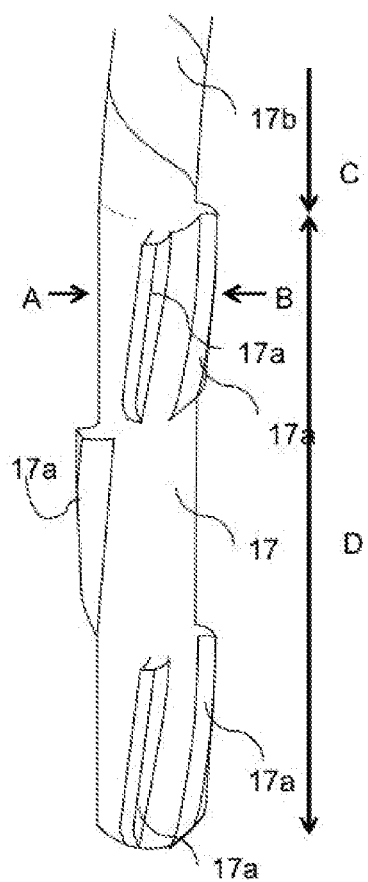
FIG. 27A is a top view of the special milling terminal, which optionally can include the invention assembly nail.
Figure 27B:
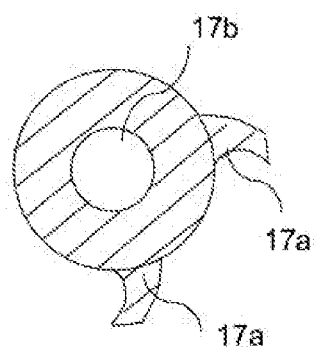
FIG. 27B is a terminal cut based on the AB cut shown in FIG. 27A.
Figure 27C:
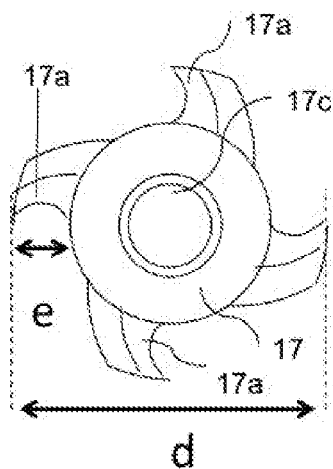
FIG. 27C is a view from below (from the distal part) of the actual terminal.

Conventional mills can be used until the nail diameter is reached, and then it is necessary to use special mills (17) comprised of three hemi-mills of two or more cutting blades (17a) each. Such hemi-mills will be placed one after the other, embedded in a rigid core so that when introduced into the femoral diaphysis, they perform as one single, complete mill with three support points in the endosteal cortex surface. This design enables the drilling or milling machine terminal to sequentially go through the screw channel. Special mills (17) are cannulated (17b) and have a flexible part (17c) in their upper section, similar to existing mills in the current state-of-the-art (FIGS. 27A-C). In FIG. 27A, the abovementioned flexible part (17c) is represented with letter C and the rigid part with letter D, showing the section which would preferably house each of them.

The diameter (d) of a conventional mill would be the effective diameter of special mills (17). The thickness (e) of a mill's cutting blades (17a) would be a third of the mill radius, that is, the sixth part of the mill's effective diameter (FIG. 27C).

This diameter (d) would be the maximum width of the special mill (17), which can therefore go through the screw channel.

For example, for a mill of 12 mm (effective diameter), the maximum width along the length of the special mill (17) would be 10 mm, meaning it would be small enough to be introduced through the channel (1d) of the cephalic screw (1) of a 10-mm nail (3). Mills (17) are introduced from the proximal femur part guided by a guide needle with olive (26).

Figure 40A:
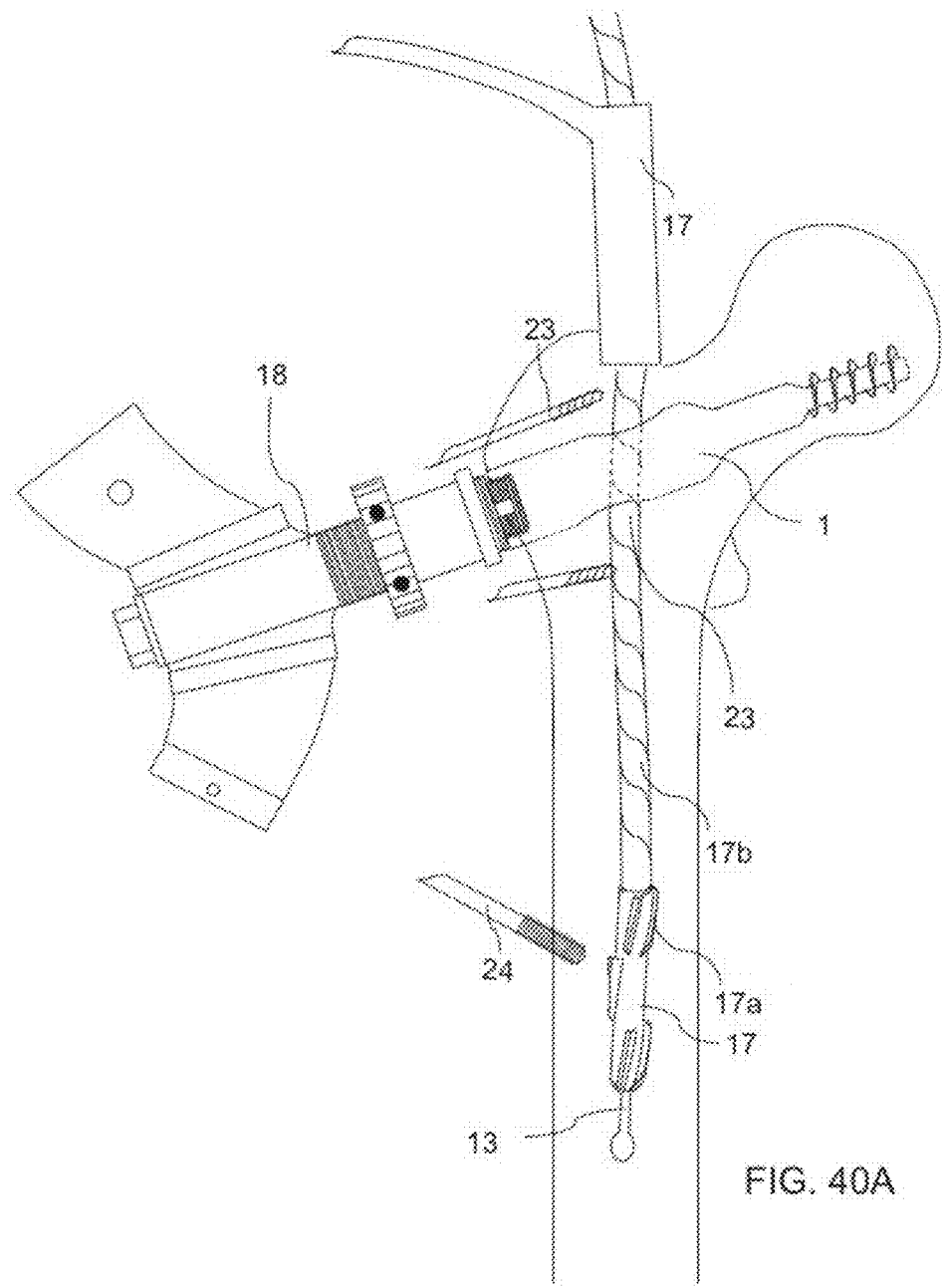
FIG. 40A is a top view of the introduction handle and cephalic screw through which the special mill penetrates around the guide needle.
Figure 40B:
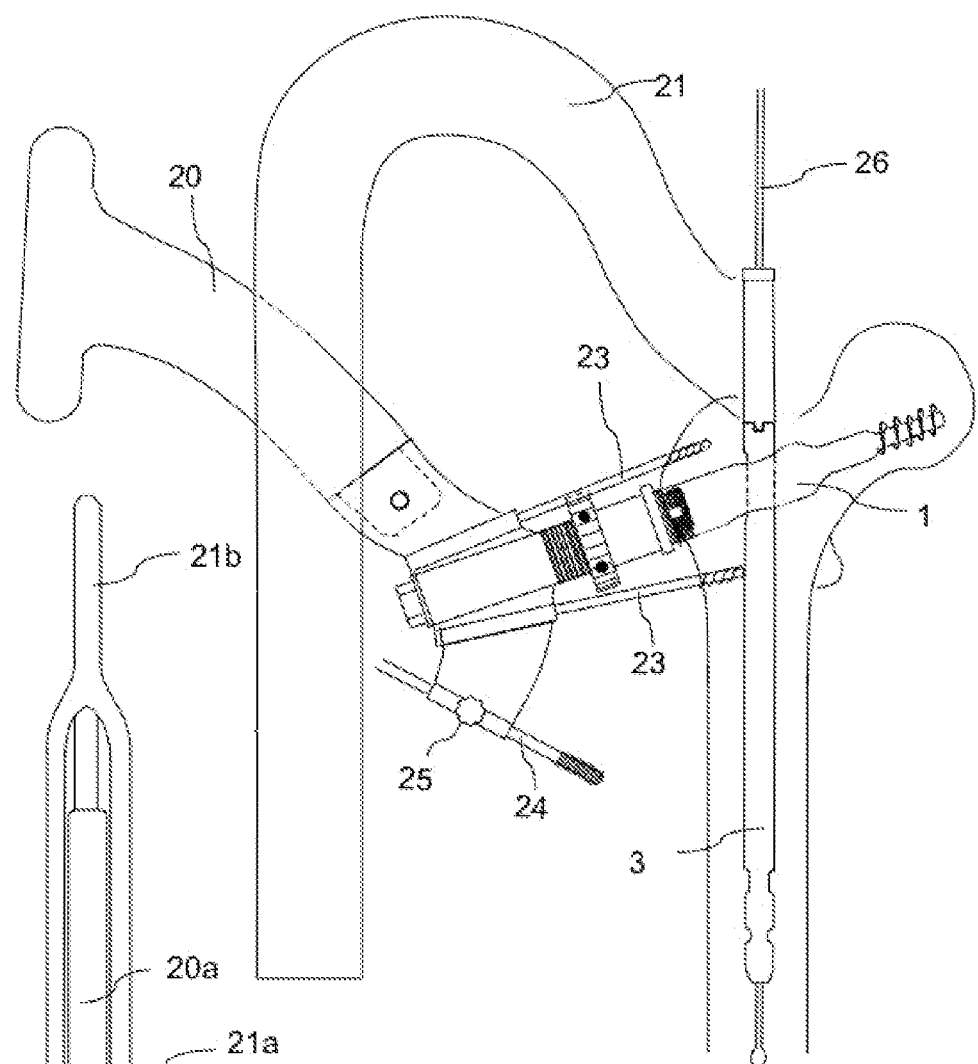
FIG. 40B is a top view of the cephalomedullary locking assembly, supported by instrumentation comprising the extender-reducer device coupled to the introduction device and the nail introduction guide.

Once drilling is completed to make a channel at a femoral neck level, the interfragmentary introduction-compression device (18) enables the introduction of the cephalic screw (1). This device (18) is joined to the cephalic screw (1) through a connector (19), as shown in FIGS. 28 through 31. The device (18) has a central core with an upper EXTENSION (18e) and an lower EXTENSION (18d), as well as five tunnels through which it is possible to introduce threaded needles (23): two upper tunnels (18a) and two lower tunnels (18b) adjacent to the central core. It also has another tunnel of larger diameter in the lowest end (18l) to place an EXTERNAL BINDING pin (24) of the Schanz type (FIG. 40). Such pin (24) is kept in place using a small bracket (25b) inserted through an orifice (18k) in the lowest end (18l) once the target reduction is achieved.

The upper extension (18e) has a void (18m) where the distal limb (20b) of the extender-reducer device (20) is placed. It also has in its front side a hole (18c) to place a second bracket (25) which will stabilize the extender through each threaded end (25a).

The central core of the interfragmentary introduction-compression device (18) has in its distal part two tabs (18j) which are inserted in the notches (1b) of the proximal part of the cephalic screw to enhance connection stability.

The distal part of central core has a broad thread (18g) of interfragmentary compression which turns manually around the external threaded surface (18h) and has a number of perforations (18n) and a small key to facilitate counter-resistance turning when needed. The distal area (18f) has a nut (18i) which turns clockwise and facilitates interfragmentary compression by pushing on the lateral femur cortex.

As for the connector (19), it has a hexagonal-shaped proximal part (19a) and a threaded distal part (19b) which adapts to the proximal part of the cephalic screw (1). A screwdriver of hexagonal-shaped tip is used to adjust it. Along its length, the connector (19) has two (upper and lower) tunnels (19c) through which the screwdriver (28) is introduced to tighten the nail-screw stabilization screws (2) of the cephalic screw (1) (FIGS. 25 through 31).

Figure 41:
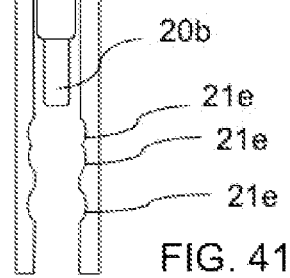

The extender-reducer device (20) is an extension of the introduction-compression device (18) (FIGS. 32 through 35) connected to it, as abovementioned, through a handle (25) in its distal limb (20b). It has a proximal "T-shaped" region (20a) which, when held, facilitates front-to-back femoral neck manipulation. When the nail (3) is inserted, this device is placed between both branches of the nail's introduction guide (21) ("fork-shaped") so that nail rotation (3) in relation to the cephalic screw (1) is stabilized to ensure stabilization screws (2) are driven to a specific longitudinal depression (3b) of the nail (3) (FIG. 41).

Figure 42:
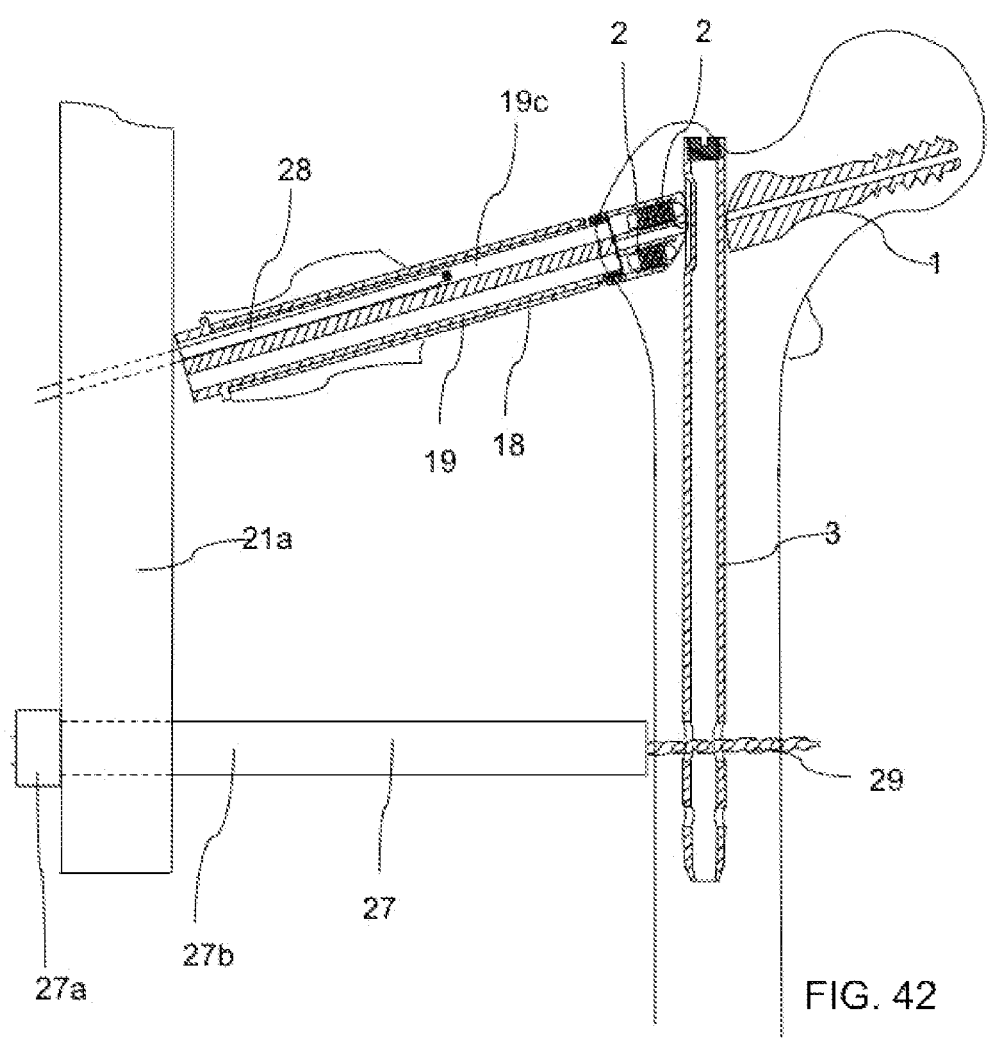
Figure 43A:
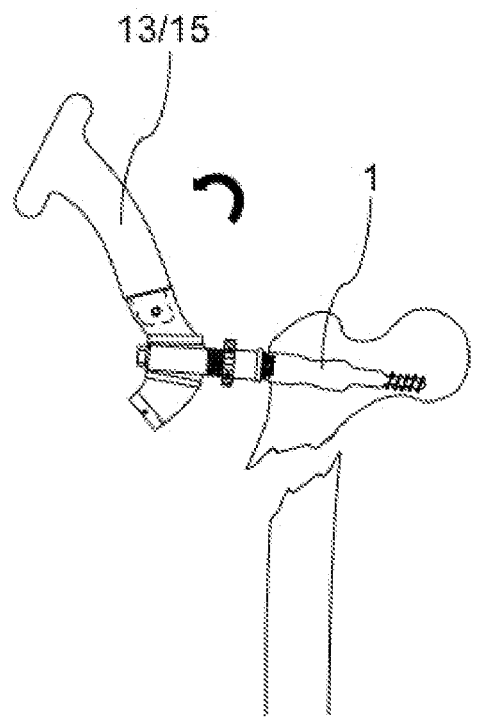
FIG. 43A shows a displaced inverted section fracture in which the cephalic screw is introduced by means of the extender-reducer device and introduction-compression device.
Figure 43B:
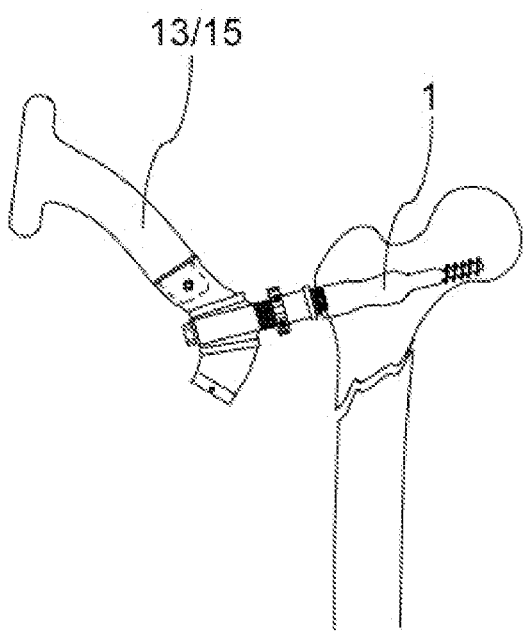
FIG. 43B shows the same fracture reduced by means of an instrumentation lever application.
Figure 44A:
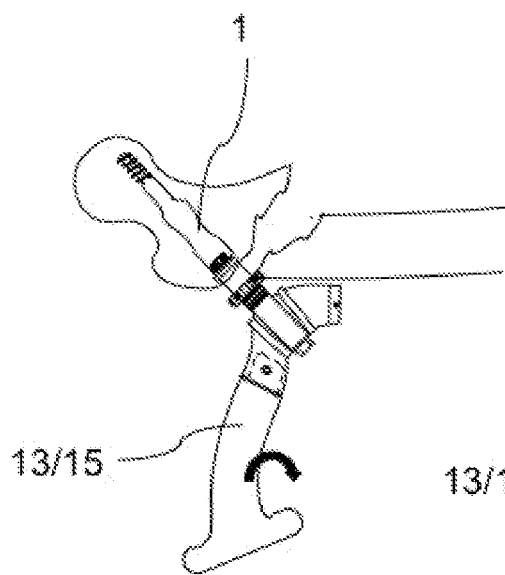
FIG. 44A shows a displaced axial plane fracture in which the cephalic screw was introduced by means of the extender-reducer device and introduction-compression device.
Figure 44B:
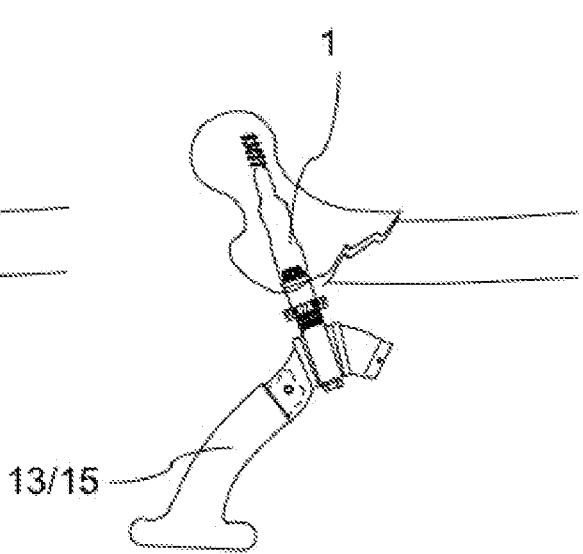
FIG. 44B shows the same fracture reduced by a clockwise rotary movement of the instrumentation.
Figure 45A:
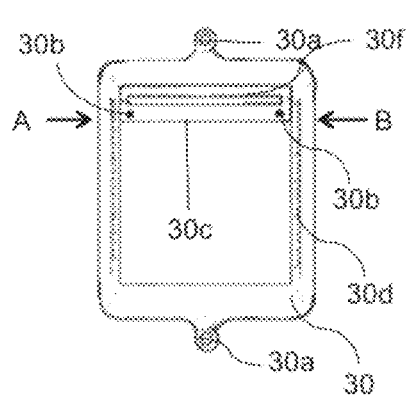
FIG. 45A is a top of the valgus-producing osteotomy device.
Figure 45B:
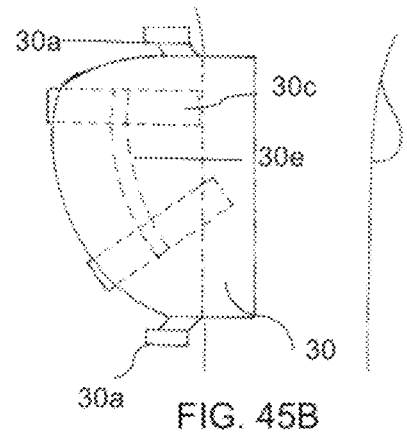
FIG. 45B is a side view of the valgus-producing osteotomy device.
Figure 46A:
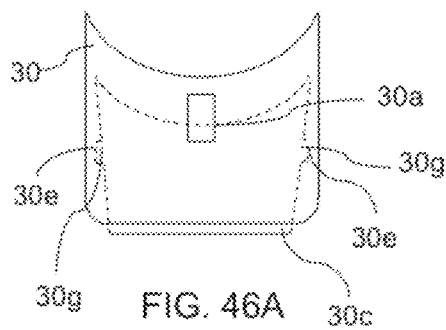
FIG. 46A is a top view of the valgus-producing osteotomy device.
Figure 46B:
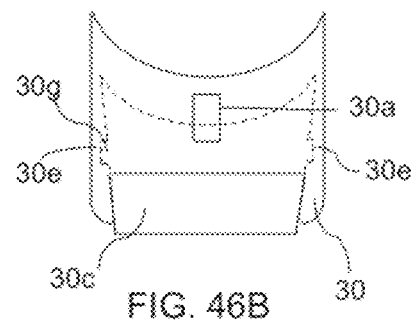
FIG. 46B is a bottom view of the valgus-producing osteotomy device.
Figure 47:
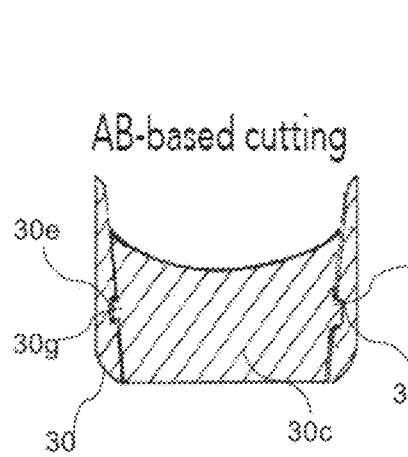
Figure 48:
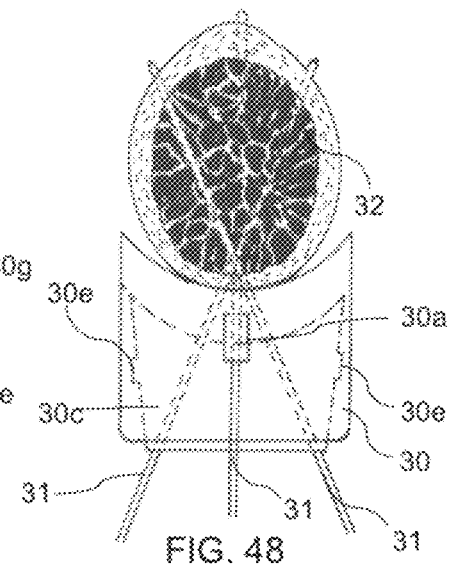

Instrumentation also includes a nail introduction guide (21) comprising a branched-off "fork-shaped" vertical part (21a) and a curved part (21b) which ends in a tubular region (21c). At the end of the tubular region there are two tabs (21d) which fit the notches (3a) of the nail (3) (FIG. 38). A guide needle (26) is introduced through the trochanteric fossa/greater trochanter tip after perforating the bone using a conventional punch. The introduction guide (21) is connected to the nail (3) by means of a connector screw (22) which has a head (22a) for an hexagonal screwdriver, a tubular part (22c) and a threaded end (22b) (FIGS. 37 & 38). The inner side of the branched-off vertical part arms (21a) of the introduction guide (21) has inner circle section depressions (21e) through which the locking guides (27) of the distal locking screws (4) are inserted. For the most proximal locking screw (4) there are two positions facilitating placement of the locking guide (27): static and dynamic, similarly to available nails in the market (FIGS. 41 & 42).

Instrumentation also includes a guide for distal locking screws (27). This guide (27) is introduced perpendicularly to the nail (3), between the branched-off vertical part arms (21a) of the nail's introduction guide (121) (FIG. 42). It has a proximal wide area (27a) and a narrow tubular section (27b) through which the drill (29) is inserted to mill the femur and enable the distal locking screw (4) to run through it. Later, the locking screw (4) is introduced through this guide using a hexagonal screwdriver.

Once the cephalic screw (1) is placed, it is possible to perform a lateral subtraction osteotomy using a valgus-producing osteotomy device (30) which adapts to the bone in the lateral region of the proximal femur and is kept in place by introducing fixation needles (31) through the fixation holes of the device (30a). The cutting guide (30c) is fixed using needles (31) inserted through convergent channel holes (30b). This insertion is initially performed horizontally to make the first cut (conventional saw) and then downwards depending on the target angulation, which can be measured through calibration (30d). Then it is refixed and the lower cut of the lateral subtraction wedge is made. This cutting guide (30c) has two edges (30g) that enable angular variation by moving through the arcuate slots (30e) of the cutting guide. It has a horizontal slot (30f) granting access to the guide through which the saw blade is introduced to make the cuts limiting the lateral subtraction wedge.

Figure 49:
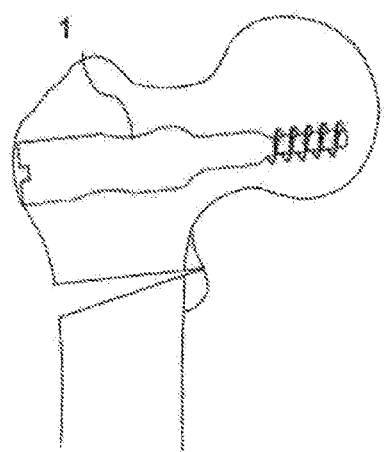
FIG. 49 represents the lateral subtraction osteotomy once the cephalic screw is placed in a femoral neck stress fracture.
Figure 50:
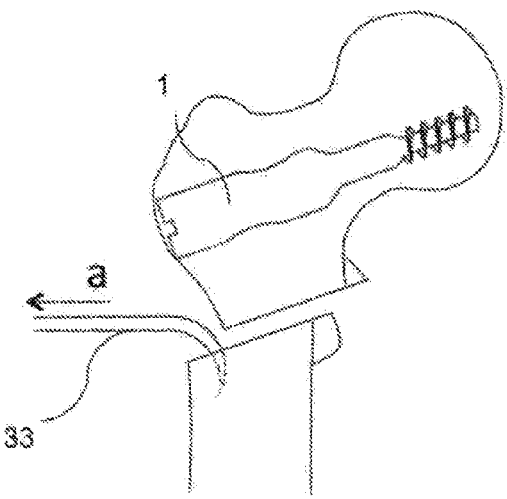
FIG. 50 shows diaphysis sliding towards the lateral region, as well as femoral neck valgus configuration after osteotomy.
Figure 51:
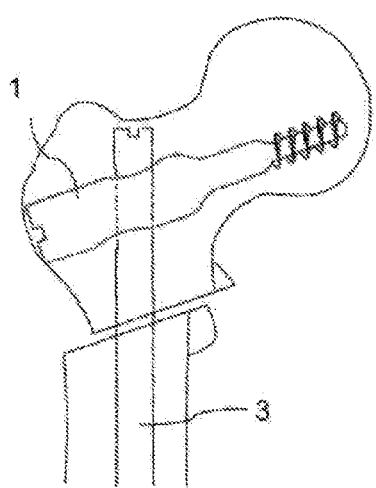
FIG. 51 represents nail introduction on reduced valgus configuration osteotomy.

Once the lateral base wedge osteotomy (FIG. 49) is made, it is recommended to move the diaphysis slightly towards the lateral region by means of a bone hook (33) to avoid mechanical limb axis alteration (FIG. 50). Later, the proximal fragment would be manipulated to reduce osteotomy's proximal and distal segments. This is done using an introduction device (18) coupled to the extender-reducer device (20). Once the reduction is completed, the nail (3) would be introduced (FIG. 51) and locked to the cephalic screw by means of stabilization screws (2) and subsequent distal locking (4).

The invention claimed is:

1. A cephalomedullary nailing system of variable angle for treating femur fractures, comprising:
   a nail;
   a cephalic screw comprising a transverse channel through which the nail is inserted and two locking screws;
   a femoral neck guide needle which is manipulated by means of a handle and has a bone support surface resembling femur anatomy;
   at least 2 upper tubular guides for anti-rotating guide needles and a lower tubular guide for a cephalic screw guide needle;
   a soft part protector having a handle and a tubular element with a distal limb equipped with stabilization gears;
   a cannulated needle reducer;
   a cephalic screw drill bit; and
   a milling system;
   wherein a geometry of the transverse channel, which is obtained by removing a geometric shape from a volume of the cephalic screw, the geometric shape corresponding to a volume that forms inside a toroidal revolution surface and a central point of the toroidal revolution surface, coincides with an axis of the cephalic screw, thereby generating, with the two locking screws, a varus-valgus stabilization system between the nail and the cephalic screw, with at least three support points.

2. The cephalomedullary nailing system of variable angle for treating femur fractures as in claim 1, wherein the nail has at least one variable morphology edge, and the cephalic screw has a slot system coinciding with edges of the nail.

3. The cephalomedullary nailing system of variable angle for treating femur fractures as in claim 1, further comprising a trochanteric support plate connected to the cephalic screw by means of a screwed device, wherein the trochanteric support plate also features screws locked to it, as well as orifices for sutures to run therethrough.

4. The cephalomedullary nailing system of variable angle for treating femur fractures as in claim 1, wherein the nail is insertable through a trochanteric fossa, and wherein there is a varus-valgus inclination range of about 100-130° between the cephalic screw and the nail, the nail being straight in its proximal part.

5. The cephalomedullary nailing system of variable angle for treating femur fractures as in claim 1, wherein the nail is insertable through a trochanter tip, and wherein there is a varus-valgus inclination range of about 70-130° between the cephalic screw and the nail, the nail being curved in its proximal part.

6. The cephalomedullary nailing system of variable angle for treating femur fractures as in claim 1, further comprising a nail introduction guide which is branched off lengthways.

7. The cephalomedullary nailing system of variable angle for treating femur fractures as in claim 1, further comprising an introduction-compression device which is coupled to a distal limb of an extender-reducer device by a handle, the extender-reducer device having a proximal T-shaped region.

8. The cephalomedullary nailing system of variable angle for treating femur fractures as in claim 1, further comprising a milling system having three hemi-mills of two or more cutting blades each, laid out one after the other and embedded in a rigid core.

9. The cephalomedullary nailing system of variable angle for treating femur fractures as in claim 1, further comprising a support attachable to a lateral femur cortex, with an angulation calibration system inside of which a saw guide moves following an arcuate trajectory.

10. Instrumentation for placement of a cephalomedullary nailing system of variable angle, comprising:

a nail;

a cephalic screw comprising a transverse channel through which the nail is inserted and two locking screws;

an interfragmentary introduction-compression device joined to the cephalic screw through a connector and having a central core with an upper extension and a lower extension, as well as five tunnels through which threaded needles can be introduced; the five tunnels comprising: two upper tunnels, two lower tunnels adjacent to the central core, as well as another tunnel of larger diameter in a lower end of the device, the tunnel of larger diameter being configured to receive a Schanz-type external binding pin;

wherein a geometry of the transverse channel, which is obtained by removing a geometric shape from a volume of the cephalic screw, the geometric shape corresponding to a volume that forms inside a toroidal revolution surface and a central point of the toroidal revolution surface, coincides with an axis of the cephalic screw, thereby generating, with the two locking screws, a varus-valgus stabilization system between the nail and the cephalic screw, with at least three support points; and wherein the external binding pin is kept in place using a small bracket inserted through an orifice in the lower end of the device.

11. A cephalomedullary nailing system of variable angle for treating femur fractures, comprising:

a nail;

a cephalic screw comprising a transverse channel through which the nail is inserted and two locking screws; and a milling system having three hemi-mills of two or more cutting blades each, laid out one after the other and embedded in a rigid core;

wherein a geometry of the transverse channel, which is obtained by removing a geometric shape from a volume of the cephalic screw, the geometric shape corresponding to a volume that forms inside a toroidal revolution surface and a central point of the toroidal revolution surface, coincides with an axis of the cephalic screw, thereby generating, with the two locking screws, a varus-valgus stabilization system between the nail and the cephalic screw, with at least three support points.

12. The cephalomedullary nailing system of variable angle for treating femur fractures, comprising:

a nail;

a cephalic screw comprising a transverse channel through which the nail is inserted and two locking screws; and a support attachable to a lateral femur cortex, with an angulation calibration system inside of which a saw guide moves following an arcuate trajectory;

wherein a geometry of the transverse channel, which is obtained by removing a geometric shape from a volume of the cephalic screw, the geometric shape corresponding to a volume that forms inside a toroidal revolution surface and a central point of the toroidal revolution surface, coincides with an axis of the cephalic screw, thereby generating, with the two locking screws, a varus-valgus stabilization system between the nail and the cephalic screw, with at least three support points.

* * * * *